(12) United States Patent
Zawel et al.

(10) Patent No.: US 10,786,491 B2
(45) Date of Patent: Sep. 29, 2020

(54) IMMUNOMODULATION BY IAP INHIBITORS

(71) Applicants: Novartis AG, Basel (CH); Dana-Farber Cancer Institute, Inc., Boston, MA (US)

(72) Inventors: Leigh Zawel, Weston, MA (US); Christopher S. Straub, Stow, MA (US); Brant G. Firestone, Westwood, MA (US); Glenn Dranoff, Lexington, MA (US); Michael Dougan, Brookline, MA (US)

(73) Assignees: NOVARTIS AG, Basel (CH); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 15/675,987

(22) Filed: Aug. 14, 2017

(65) Prior Publication Data
US 2017/0368047 A1    Dec. 28, 2017

Related U.S. Application Data

(62) Division of application No. 12/992,631, filed as application No. PCT/US2009/043874 on May 14, 2009, now Pat. No. 9,750,729.

(60) Provisional application No. 61/053,947, filed on May 16, 2008.

(51) Int. Cl.
| | |
|---|---|
| A61K 39/39 | (2006.01) |
| A61K 31/427 | (2006.01) |
| A61K 31/4439 | (2006.01) |
| A61K 31/421 | (2006.01) |
| A61K 31/506 | (2006.01) |
| A61K 39/00 | (2006.01) |
| C12N 5/078 | (2010.01) |

(52) U.S. Cl.
CPC ........ *A61K 31/4439* (2013.01); *A61K 31/421* (2013.01); *A61K 31/427* (2013.01); *A61K 31/506* (2013.01); *A61K 39/0011* (2013.01); *A61K 39/39* (2013.01); *A61K 2039/55511* (2013.01); *A61K 2039/80* (2018.08); *C12N 5/0634* (2013.01)

(58) Field of Classification Search
CPC .. A61K 31/427; A61K 31/4439; A61K 39/39; A61K 2039/55511; A61K 2039/80; C12N 5/0634
See application file for complete search history.

(56) References Cited

U.S. PATENT DOCUMENTS

| | | | |
|---|---|---|---|
| 4,965,250 A | 10/1990 | Vincent | |
| 6,107,041 A * | 8/2000 | Korneluk | A61K 38/1709 |
| | | | 435/320.1 |
| 2005/0197403 A1 | 9/2005 | Harran | |
| 2005/0234042 A1 * | 10/2005 | Palermo | C07D 207/06 |
| | | | 514/215 |
| 2008/0234042 A1 | 9/2008 | Uemura et al. | |
| 2014/0004101 A1 | 1/2014 | Chen et al. | |

FOREIGN PATENT DOCUMENTS

| | | | |
|---|---|---|---|
| FR | 2610934 | 8/1988 | |
| WO | 2008077969 | 8/2005 | |
| WO | 2005084317 | 9/2005 | |
| WO | 2005094818 | 10/2005 | |
| WO | 2005097791 | 10/2005 | |
| WO | 2006091972 | 8/2006 | |
| WO | 2007075525 | 7/2007 | |
| WO | 2008014236 | 1/2008 | |
| WO | 2008016893 | 2/2008 | |
| WO | 2008045905 | 4/2008 | |
| WO | 2008057172 | 5/2008 | |
| WO | WO-2008057172 A2 * | 5/2008 | ........... G01N 33/574 |
| WO | 2008067280 | 6/2008 | |
| WO | 2008109057 | 9/2008 | |

OTHER PUBLICATIONS

STN Registry database compound 1005342-46-0 (entered STN Feb. 25, 2008). (Year: 2008).*
Suggitt and Bibby, "50 Years of Preclinical Anticancer Drug Screening: Empirical to Target-Driven Approaches," Clinical Cancer Research, vol. 11, (2005), pp. 971-981.
Sausville and Burger, "Contributions of Human Tumor Xenografts to Anticancer Drug Development," Cancer Res, vol. 66, No. 7, (2006), pp. 3351-3354.
Brosssart et al., "The Epithelial Tumor Antigen MUC1 is Expressed in Hematological Malignancies and is Recognized by MUC1-Specific Cytotoxic T-Lymphocytes," Cancer Research, vol. 61, (2001), pp. 6846-6850.
Extended European Search Report, issued in corresponding Application No. 13178264.1, dated Jan. 20, 2014.
Greenberg and Riddell, "Deficient Cellular Immunity—Finding and Fixing the Defects," Science, vol. 285, (1999), pp. 546-551.
International Search Report and Written Opinion, issued in PCT/US2009/043874, dated Aug. 12, 2009.
Extended European Search Report dated Jul. 17, 2020 from corresponding EP Application No. 20159523.8 (10 pages—English language).

* cited by examiner

*Primary Examiner* — Theodore R. West
(74) *Attorney, Agent, or Firm* — Brinks Gilson & Lione; Yuezhong Feng

(57) ABSTRACT

The present invention is directed to immune adjuvants containing IAP inhibitors, including Smac mimetics. The invention further provides pharmaceutical compositions and vaccines containing an IAP inhibitor and an antigen. Methods of enhancing an immune response by administration of an IAP inhibitor, methods of treating or preventing cancer, methods of treating or preventing infections, methods of treating autoimmune disorders, and methods of potentiating cytokine or antibody production are also provided.

6 Claims, 15 Drawing Sheets

IMMUNOMODULATION BY IAP INHIBITORS

This application is a divisional of U.S. application Ser. No. 12/992,631, filed Feb. 21, 2011, the entire contents of which are hereby incorporated herein by reference. U.S. application Ser. No. 12/992,631 is a National Stage application of International Application No. PCT/US2009/043874, filed May 14, 2009, which claims the benefit of U.S. Provisional Application No. 61/053,947, filed May 16, 2008, the entire contents of both of which are hereby incorporated herein by reference.

BACKGROUND OF THE INVENTION

Immunization is the process of administering antigenic material (e.g., a vaccine) to produce or artificially increase an immune response. One frequently encountered problem is that many antigens used for immunization are not sufficiently immunogenic to raise an antibody titer sufficient to provide protection against future challenge. Weak antigens may also be deficient in inducing cell-mediated immunity.

To strengthen the humoral and/or cellular immune response to an antigen, it is common to administer an antigen in conjunction with an adjuvant. An adjuvant is a substance that enhances the immune response to an antigen. Administration of an adjuvant with an antigen may cause an individual to respond to an antigen who otherwise would not respond in the absence of the adjuvant. Commonly used adjuvants include Freund's adjuvant, Keyhole Limpet Hemocyanin (KLH), and granulocyte-macrophage colony stimulating factor (GM-CSF). Despite the immune-enhancing properties of known adjuvants, these adjuvants remain insufficient to induce an immune response in a subject against many clinically important antigens, for example, tumor associated antigens.

Accordingly, there is a need for new adjuvant compositions.

SUMMARY OF THE INVENTION

The present invention pertains to adjuvants possessing improved immunogenic properties. These immune adjuvants are capable of broadly enhancing immune cell activation. In at least one embodiment, the present invention pertains to the unexpected discovery that inhibitors of the IAP (Inhibitor of Apoptosis) protein family function as potent immune adjuvants capable of enhancing physiologically relevant activation signals in diverse lineages of immune cells. Accordingly, the invention features, in a first aspect, an immune adjuvant comprising an IAP inhibitor capable of modulating immune activity. In one embodiment, the IAP inhibitor is a compound of Formula I. In another embodiment, the IAP inhibitor is a compound of Formula II. In exemplary embodiments, the IAP inhibitor is (N-[1-cyclohexyl-2-oxo-2-(6-phenethyl-octahydro-pyrrolo[2,3-c]pyridin-1-yl)-ethyl]-2-methylamino-propionamide).

In another aspect, the invention features a pharmaceutical composition comprising an immunogenic quantity of an antigen and an adjuvant, wherein the adjuvant comprises an IAP inhibitor. In a related aspect, the invention features a vaccine comprising an immunogenic quantity of an antigen and an adjuvant, wherein the adjuvant comprises an IAP inhibitor. In one embodiment of these aspects, the IAP inhibitor is a compound of Formula I. In another embodiment of these aspects, the IAP inhibitor is a compound of Formula II. In exemplary embodiments, the IAP inhibitor is N-[1-cyclohexyl-2-oxo-2-(6-phenethyl-octahydro-pyrrolo[2,3-c]pyridin-1-yl)-ethyl]-2-methylamino-propionamide.

The invention further features a method of enhancing an immune response of a subject, by administering to the subject an immune enhancing amount of an IAP inhibitor. In a preferred embodiment, an immune enhancing amount of an IAP inhibitor is a therapeutically effective amount. In one embodiment, the immune response is mediated by one or more immune cell types selected from the group consisting of dendritic cells, B cells, T cells (e.g., CD4+ T cells, CD8+ T cells, NKT cells, etc.), NK cells, and macrophages. In yet another aspect, provided herein is a use of an IAP inhibitor for the manufacture of a medicament for enhancing an immune response in a subject.

In a related aspect, the invention features a method of enhancing an immune response of a subject to an antigen, comprising the steps of (a) administering to the subject an immunogenic quantity of an antigen; and (b) administering an immune enhancing amount of an IAP inhibitor. In one embodiment, the immune response is mediated by one or more immune cell types selected from the group consisting of dendritic cells, B cells, T cells (e.g., CD4+ T cells, CD8+ T cells, and NKT cells), NK cells, and macrophages. In another embodiment of this aspect, the antigen and the IAP inhibitor are administered sequentially. In an alternative embodiment, the antigen and the IAP inhibitor are administered simultaneously. The antigen and the IAP inhibitor may be administered as a single composition, or as separate compositions. In another embodiment, the antigen is a tumor-derived antigen or tumor antigen. In another embodiment, the antigen comprises a pathogen, an attenuated pathogen, or a portion thereof. In another embodiment, the antigen comprises a mammalian, plant, viral, bacterial or fungal antigen. In one embodiment, the antigen is a polypeptide molecule. In another embodiment, the antigen is a nucleic acid molecule. In yet another aspect, provided herein is a use of an IAP inhibitor for the manufacture of a medicament for enhancing an immune response of a subject to an antigen.

The invention further features a method of treating a cancer in a subject, which comprises administering to the subject in need thereof a therapeutically effective amount of an IAP inhibitor and an immunogenic quantity of an antigen, wherein administration of the IAP inhibitor and the antigen enhances the immune response of the subject to the cancer. In one embodiment, the cancer is a solid tumor. In another embodiment, the cancer is a hematologic malignancy. In one embodiment, the antigen comprises a cancer cell. In an exemplary embodiment, the cancer cell is obtained from the subject. In another exemplary embodiment, the cancer cell is proliferation incompetent. In one embodiment of this aspect, the antigen and the IAP inhibitor are administered sequentially. In an alternative embodiment, the antigen and the IAP inhibitor are administered simultaneously. The antigen and the IAP inhibitor may be administered as a single composition or as separate compositions. In yet another aspect, provided herein is a use of an IAP inhibitor for the manufacture of a medicament for treating cancer in a subject.

In another embodiment, the invention features a method of treating an infection caused by an infectious agent, which comprises administering to a subject in need thereof a therapeutically effective amount of an IAP inhibitor and an immunogenic quantity of an antigen, wherein administration of said IAP inhibitor and said antigen enhances the immune response of the subject to the infectious agent. In one embodiment, the infectious agent is selected from a bacterium, a virus, a protozoan, a fungus, and a parasite. In another embodiment, the antigen and the IAP inhibitor are administered sequentially. In an alternative embodiment, the antigen and the IAP inhibitor are administered simultaneously. The antigen and the IAP inhibitor may be administered as a single composition or as separate compositions. In yet another aspect, provided herein is a use of an IAP inhibitor for the manufacture of a medicament for treating infection in a subject.

The invention further features a method of treating an autoimmune disorder in a subject, comprising administering to the subject a composition comprising an IAP inhibitor, such that the autoimmune disorder is treated. In one embodiment of this aspect, the autoimmune disorder is reactive arthritis or autoimmunity associated with HIV. In yet another aspect, provided herein is a use of an IAP inhibitor for the manufacture of a medicament for treating an autoimmune disorder in a subject.

In another aspect, the invention features a method of enhancing an immune activity of an activated immune cell, comprising contacting an activated immune cell with an IAP inhibitor. In one embodiment, the immune activity comprises potentiating proliferation. In another embodiment, the immune activity comprises potentiating cytokine production. In one aspect of these embodiments, the activated immune cell is selected from the group consisting of dendritic cells, B cells, T cells (e.g., CD4+ T cells, CD8+ T cells, and NKT cells), NK cells, and macrophages. In another embodiment, the immune activity comprises potentiating antibody production. In one aspect of this embodiment, the activated immune cell is selected from the group consisting of a B-cell, a plasma cell, and a hybridoma cell. In one embodiment, contacting an activated immune cell with an IAP inhibitor comprises administering the IAP inhibitor to a subject. In yet another aspect, provided herein is a use of an IAP inhibitor for the manufacture of a medicament for enhancing an immune activity of an activated immune cell.

In one embodiment of each of the foregoing aspects of the invention, the IAP inhibitor is a compound of Formula I or Formula II. In another embodiment of each of the foregoing aspects of the invention, the IAP inhibitor is a compound of Formula II. In exemplary embodiments, the IAP inhibitor is N-[1-cyclohexyl-2-oxo-2-(6-phenethyl-octahydro-pyrrolo[2,3-c]pyridin-1-yl)-ethyl]-2-methylamino-propionamide.

The present invention further provides kits containing an IAP inhibitor. In one aspect, the invention features a kit comprising (a) a pharmaceutical composition comprising an IAP inhibitor and a pharmaceutically acceptable carrier; (b) a packaging material enclosing said pharmaceutical composition; and (c) instructions for use of said pharmaceutical composition for the enhancement of an immune response of a subject. In one embodiment, the instructions indicate that the pharmaceutical composition is to be administered to the subject with an antigen. In another embodiment, the kit further comprises an antigen. In one embodiment, the kit contains instructions for use of said pharmaceutical composition in the treatment of cancer in a subject in need thereof. In an exemplary embodiment of this aspect, the IAP inhibitor is a compound of Formula I or Formula II. In another exemplary embodiment, the IAP inhibitor is (N-[1-cyclohexyl-2-oxo-2-(6-phenethyl-octahydro-pyrrolo[2,3-c]pyridin-1-yl)-ethyl]-2-methylamino-propionamide.

BRIEF DESCRIPTION OF THE DRAWINGS

FIG. 2A depicts data, which indicates that inhibition of IAP family members does not sensitize mature CD4+ T cells to apoptosis, namely cell counts after 24 hours.

FIG. 2B depicts data, which indicates that inhibition of IAP family members does not sensitize mature CD4+ T cells to apoptosis, namely treatment did not alter the total number of T cells nor did it contribute to apoptosis.

DETAILED DESCRIPTION OF THE INVENTION

Figure 1A:
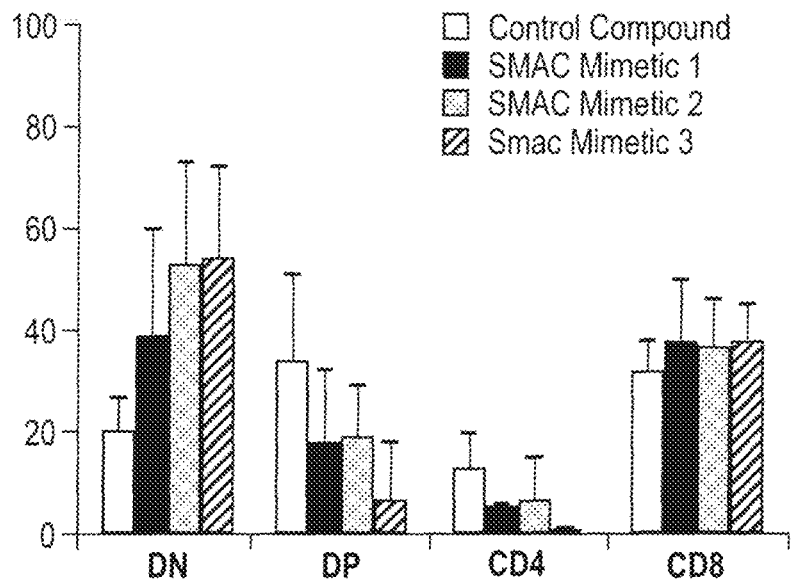
FIG. 1A depicts data, which indicates that NKT cell development in fetal thymic organ culture (FTOC) is blocked by treatment with IAP inhibitors, namely treatment with FTOCs with IAP inhibitors led to moderate decrease in CD4+ T cells with no consistent effect on culture size of on CD8+ and double positive T cells.

The present invention is based, at least in part, on the surprising discovery that IAP inhibitors function as potent immune adjuvants capable of enhancing physiologically relevant activation signals in diverse lineages of immune cells. These compounds did not alter the function of resting immune cells, but did enhance immune cell activation in the context of stimulation. This activation is evidenced by, for example, increased expansion and cytokine production. This property of IAP inhibitors positions these compounds as ideal agents for the promotion of immunity, with numerous clinical applications.

Various aspects of the invention are described in further detail in the following subsections. Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice of the invention, examples of suitable methods and materials are described below. The materials, methods, and examples described herein are illustrative only and are not intended to be limiting. All publications, patent applications, patents, and other references mentioned herein are incorporated by reference in their entirety.

I. IAP Inhibitors

Apoptosis, a process of programmed cell death, is tightly orchestrated by a series of molecular events. Principle effectors of apoptotic cell death are the caspases, a family of cysteine proteases that preferentially cleave target peptides adjacent to aspartate residues. In a non-apoptotic cell, caspases are retained in an inactive state. A pro-apoptotic stimulus triggers the activation of a hierarchical caspase cascade, leading to proteolytic cleavage of essential cellular proteins and ultimately cell death.

Activation of caspases is stringently controlled by a number of cellular factors. Members of the IAP (inhibitor of apoptosis) protein family bind directly to caspases, and this binding suppresses caspase activity. Binding to caspases is mediated by the IAP BIR (baculovirus IAP repeat) domains, which are essential for the anti-apoptotic activity of IAPs. The IAP family contains the prototypical family members XIAP, cIAP-1 and cIAP-2, and also includes, for example, NAIP (neuronal apoptosis inhibitor protein), ML-IAP (melanoma IAP), ILP-2 (IAP-like protein 2) and Op-IAP (a baculoviral IAP).

A number of factors have been identified that further mediate the apoptotic pathway by suppressing the activity of IAPs. Most prominent among these are Smac (second mitochondrial activator of caspases) and the murine Smac ortholog DIABLO (direct IAP binding protein with low pI), which localize to the mitochondria and are released into the cytosol in response to apoptotic stimuli. Smac/DIABLO inhibits the activity of IAP proteins by binding directly to IAPs and precluding IAP interaction with caspases. The discovery that IAP family members are overexpressed in numerous types of cancer led researchers to hypothesize that IAP inhibitors may have clinical significance as anti-cancer agents by promoting pro-apoptotic signaling in cancer cells. The present invention is based, at least in part, on the unexpected discovery that IAP inhibitors are additionally useful as immune adjuvants capable of enhancing an immune response.

Numerous IAP inhibitors including Smac mimetics have been developed which likewise interact with IAPs and inhibit their activity. Accordingly, an "IAP inhibitor" refers to any compound that inhibits the activity of a member of the IAP family. Such compounds may include, for example, small molecules, polypeptides (i.e., Smac mimetic peptides), RNA interference molecules targeting IAP proteins (e.g. siRNA or antisense RNA), and anti-IAP antibodies.

In particular embodiments, an IAP inhibitor of the invention is a compound of Formula I:

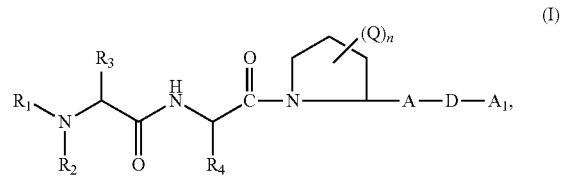

and pharmaceutically acceptable salts, enantiomers, stereoisomers, rotamers, tautomers, diastereomers, or racemates thereof;

wherein $R_1$ is H, $C_1$-$C_4$ alkyl, $C_2$-$C_4$ alkenyl, $C_2$-$C_4$ alkynyl or $C_3$-$C_{10}$ cycloalkyl, wherein $R_1$ may be unsubstituted or substituted;

$R_2$ is H, $C_1$-$C_4$ alkyl, $C_2$-$C_4$ alkenyl, $C_2$-$C_4$ alkynyl, $C_3$-$C_{10}$ cycloalkyl, wherein $R_2$ may be unsubstituted or substituted;

$R_3$ is H, $CF_3$, $C_2F_5$, $C_1$-$C_4$ alkyl, $C_2$-$C_4$ alkenyl, $C_2$-$C_4$ alkynyl, $CH_2$—Z, or $R_2$ and $R_3$, taken together with the nitrogen atom to which they are attached, form a heterocyclic ring, wherein the alkyl, alkenyl, alkynyl groups or het ring may be unsubstituted or substituted;

Z is H, OH, F, Cl, $CH_3$, $CH_2Cl$, $CH_2F$ or $CH_2OH$;

$R_4$ is $C_{1-10}$ alkyl, $C_{1-10}$ alkenyl, $C_{1-10}$ alkynyl, $C_3$-$C_{10}$ cycloalkyl, wherein the $C_{1-10}$ alkyl, or cycloalkyl groups are unsubstituted or substituted;

A is het, which may be substituted or unsubstituted;

D is $C_1$-$C_7$ alkylene or $C_2$-$C_9$ alkenylene, C(O), O, $NR_7$, $S(O)_r$, C(O)—$C_1$-$C_{10}$ alkyl, O—$C_1$-$C_{10}$ alkyl, $S(O)_r$—$C_1$-$C_{10}$ alkyl, $C(O)C_0$-$C_{10}$ arylalkyl, $OC_0$-$C_{10}$ arylalkyl, or $S(O)_r$ $C_0$-$C_{10}$ arylalkyl, wherein alkyl and aryl groups may be unsubstituted or substituted;

r is 0, 1 or 2;

$A_1$ is a substituted or unsubstituted aryl or unsubstituted or substituted het, wherein substituents on aryl and het are halo, alkyl, lower alkoxy, $NR_5R_6$, CN, $NO_2$ or $SR_5$;

each Q is independently H, $C_1$-$C_{10}$ alkyl, $C_1$-$C_{10}$ alkoxy, aryl $C_1$-$C_{10}$ alkoxy, OH, O—$C_1$-$C_{10}$ alkyl, $(CH_2)_{0-6}$—$C_3$-$C_7$ cycloalkyl, aryl, aryl $C_1$-$C_{10}$ alkyl, O—$(CH_2)_{0-6}$ aryl, $(CH_2)_{1-6}$ het, het, O—$(CH_2)_{1-6}$ het, —$OR_{11}$, $C(O)R_{11}$, —$C(O)N(R_{11})(R_{12})$, $N(R_{11})(R_{12})$, $SR_{11}$, $S(O)R_{11}$, $S(O)_2R_{11}$, $S(O)_2$—$N(R_{11})(R_{12})$, or $NR_{11}$—$S(O)_2$—$(R_{12})$, wherein alkyl, cycloalkyl and aryl are unsubstituted or substituted;

n is 0, 1, 2 or 3, 4, 5, 6 or 7;

$R_{11}$ and $R_{12}$ are independently H, $C_1$-$C_{10}$ alkyl, $(CH_2)_{0-6}$—$C_3$-$C_7$ cycloalkyl, $(CH_2)_{0-6}$—$(CH)_{0-1}(aryl)_{1-2}$, C(O)—$C_1$-$C_{10}$ alkyl, —C(O)—$(CH_2)_{1-6}$—$C_3$-$C_7$ cycloalkyl, —C(O)—O—$(CH_2)_{0-6}$-aryl, —C(O)—$(CH_2)_{0-6}$—O-fluorenyl, C(O)—NH—$(CH_2)_{0-6}$-aryl, C(O)—$(CH_2)_{0-6}$-aryl, C(O)—$(CH_2)_{1-16}$-het, —C(S)—$C_1$-$C_{10}$ alkyl, —C(S)—$(CH_2)_{1-6}$—$C_3$-$C_7$ cycloalkyl, —C(S)—O—$(CH_2)_{0-6}$-aryl, —C(S)—$(CH_2)_{0-6}$—O-fluorenyl, C(S)—NH—$(CH_2)_{0-6}$-aryl, —C(S)—$(CH_2)_{0-6}$-aryl or C(S)—$(CH_2)_{1-6}$-het, $C(O)R_{15}$, $C(O)NR_{15}R_{16}$, $C(O)OR_{15}$, $S(O)_mR_{15}$, $S(O)_mNR_{15}R_{16}$, m=1 or 2, $C(S)R_{15}$, $C(S)NR_{15}R_{16}$, $C(S)OR_{15}$, wherein alkyl, cycloalkyl and aryl are unsubstituted or substituted; or $R_{11}$ and $R_{12}$ are a substituent that facilitates transport of the molecule across a cell membrane, or $R_{11}$ and $R_{12}$ together with the nitrogen atom form het, wherein the alkyl substituents of $R_{11}$ and $R_{12}$ may be unsubstituted or substituted by one or more substituents selected from $C_1$-$C_{10}$ alkyl, halogen, OH, O—$C_1$-$C_6$ alkyl, —S—$C_1$-$C_6$ alkyl, $CF_3$ or $NR_{15}R_{16}$;

substituted cycloalkyl substituents of $R_{11}$ and $R_{12}$ are substituted by one or more substituents selected from a $C_2$-$C_{10}$ alkene; $C_1$-$C_6$ alkyl; halogen; OH; O—$C_1$-$C_6$ alkyl; S—$C_1$-$C_6$ alkyl, $CF_3$; or $NR_{15}R_{16}$ and substituted het or substituted aryl of $R_{11}$ and $R_{12}$ are substituted by one or more substituents selected from halogen, hydroxy, $C_1$-$C_4$ alkyl, $C_1$-$C_4$ alkoxy, nitro, CNO—C(O)—$C_1$-$C_4$alkyl and C(O)—O—$C_1$-$C_4$-alkyl;

$R_5$, $R_6$ and $R_7$ are independently hydrogen, lower alkyl, aryl, aryl lower alkyl, cycloalkyl, or cycloalkyl lower alkyl, $C(O)R_{15}$, $S(O)R_{15}$, $C(O)OR_{15}$, $C(O)NR_{15}R_{16}$; and the substituents on $R_1$, $R_2$, $R_3$, $R_4$, Q, and A and $A_1$ groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, aryl-sulfonyl, aryl-lower alkylsulfonyl, lower aryl alkyl lower alkylarylsulfonyl, halogen-lower alkylmercapto, halogen-lower alkylsulfonyl, phosphono (—P(=O)($OH)_2$), hydroxy-lower alkoxy phosphoryl or di-lower alkoxyphosphoryl, $(R_9)NC(O)$—$NR_{10}R_{13}$, lower alkyl carbamic acid ester or carbamates or —$NR_8R_{14}$, wherein $R_8$ and $R_{14}$ can be the same or different and are independently H or lower alkyl, or $R_8$ and $R_{14}$, together with the N atom, form a 3- to 8-membered heterocyclic ring containing nitrogen heteroring atoms and may optionally contain one or two additional heteroring atoms selected from nitrogen, oxygen and sulfur, wherein the heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbarmoyl, N-lower or N,N-dilower alkyl carbamoyl, mercapto, or lower alkylthio;

$R_9$, $R_{10}$ and $R_{13}$ are independently hydrogen, lower alkyl, halogen substituted lower alkyl, aryl, aryl lower alkyl, halogen substituted aryl, halogen substituted aryl lower alkyl, $R_{15}$ and $R_{16}$ are independently hydrogen, lower alkyl, aryl, aryl lower alkyl, cycloalkyl, or cycloalkyl lower alkyl, and het is a 5- to 7-membered monocyclic heterocyclic ring containing 1-4 heteroring atoms selected from N, O and S or an 8- to 12-membered fused ring system that includes one 5- to 7-membered monocyclic heterocyclic ring containing 1, 2 or 3 heteroring atoms selected from N, O and S, wherein het is unsubstituted or substituted.

In another embodiment, the IAP inhibitor is a compound of Formula II:

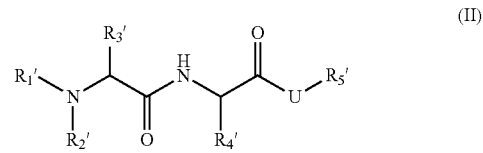

(II)

and pharmaceutically acceptable salts, enantiomers, stereoisomers, rotamers, tautomers, diastereomers, or racemates thereof, wherein $R_1'$ is H;

$R_2'$ is $C_1$-$C_4$ alkyl; which may be unsubstituted or substituted;

$R_3'$ is $C_1$-$C_4$ alkyl;

$R_4'$ is —$C_3$-$C_{10}$ cycloalkyl; which may be unsubstituted or substituted;

$R_5'$ is H; $C_1$-$C_{10}$-alkyl; aryl; phenyl; $C_3$-$C_7$cycloalkyl; —$(CH_2)_{1-6}$—$C_3$-$C_7$cycloalkyl; —$C_1$-$C_{10}$ alkyl-aryl; —$(CH_2)_{0-6}$—$C_3$-$C_7$cycloalkyl-$(CH_2)_{0-6}$-phenyl; —$(CH_2)_{0-4}$CH—$((CH_2)_{1-4}$-phenyl$)_2$; —$(CH_2)_{0-6}$—CH(phenyl$)_2$; -indanyl; —C(O)—$C_1$-$C_{10}$ alkyl; —C(O)—$(CH_2)_{1-6}$—$C_3$-$C_7$-cycloalkyl; —C(O)—$(CH_2)_{0-6}$-phenyl; —$(CH_2)_{0-6}$—C(O)-phenyl; —$(CH_2)_{0-6}$-het; —C(O)—$(CH_2)_{1-6}$-het; or $R_5'$ is a residue of an amino acid, wherein the alkyl, cycloalkyl, phenyl and aryl substituents are unsubstituted or substituted;

U is as shown in structure III:

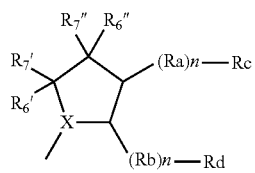

wherein
$R_5'$ is attached to Rc or Rd;
each n is, independently, 0-5;
X is C or N;
Ra and Rb are independently an O, S, or N atom or $C_{0-8}$ alkyl wherein one or more of the carbon atoms in the alkyl chain may be replaced by a heteroatom selected from O, S or N, and where the alkyl may be unsubstituted or substituted; Rd is selected from:

—Re-Q-(Rf)$_p$(Rg)$_q$; or                (a)

Ar$_1$-D-Ar$_2$;                              (b)

Rc is H or Rc and Rd may together form a cycloalkyl or het; where if Rd and Rc form a cycloalkyl or het, $R_5'$ is attached to the formed ring at a C or N atom;
p and q are independently 0 or 1;
Re is $C_{1-8}$ alkyl or alkylidene, and Re which may be unsubstituted or substituted;
Q is N, O, S, S(O), or S(O)$_2$;
Ar$_1$ and Ar$_2$ are substituted or unsubstituted aryl or het;
Rf and Rg are each independently H; —$C_1$-$C_{10}$ alkyl; $C_1$-$C_{10}$alkylaryl; —OH; —O—$C_1$-$C_{10}$ alkyl; —(CH$_2$)$_{0-6}$—$C_3$-$C_7$cycloalkyl; —O—(CH$_2$)$_{0-6}$-aryl; phenyl; aryl; phenyl-phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S—R$_{11}$; —S(O)—R$_{11}$; —S(O)$_2$—R$_{11}$; —S(O)$_2$—NR$_{11}$R$_{12}$; —NR$_{11}$—S(O)$_2$—R$_{12}$; S—$C_1$-$C_{10}$ alkyl; aryl-$C_1$-$C_4$alkyl; het-$C_1$-$C_4$-alkyl wherein alkyl, cycloalkyl, het and aryl are unsubstituted or substituted; —SO$_2$—$C_1$-$C_2$alkyl; —SO$_2$—$C_1$-$C_2$alkylphenyl; —O—$C_1$-$C_4$alkyl; or R$_g$ and R$_f$ form a ring selected from het or aryl;
D is —CO—; —C(O)—$C_{1-7}$ alkylene or arylene; —CF$_2$—; —O—; —S(O)$_r$ where r is 0-2; 1,3-dioxaolane; or $C_{1-7}$ alkyl-OH; where alkyl, alkylene or arylene may be unsubstituted or substituted with one or more halogens, OH, —O—$C_1$-$C_6$alkyl, —S—$C_1$-$C_6$alkyl or —CF$_3$; or D is —N(Rx)- wherein Rx is H; $C_{1-7}$ alkyl (unsubstituted or substituted); aryl; —O($C_{1-7}$cycloalkyl) (unsubstituted or substituted); C(O)—$C_1$-$C_{10}$ alkyl; C(O)—$C_0$-$C_{10}$ alkyl-aryl; C—O—$C_1$-$C_{10}$ alkyl; C—O—$C_0$-$C_{10}$ alkyl-aryl or SO$_2$—$C_1$-$C_{10}$-alkyl; SO$_2$—($C_0$-$C_{10}$-alkylaryl);
$R_6''$, $R_7''$, $R_6'$ and $R_7'$ are each independently H; —$C_1$-$C_{10}$ alkyl; —$C_1$-$C_{10}$ alkoxy; aryl-$C_1$-$C_{10}$ alkoxy; —OH; —O—$C_1$-$C_{10}$ alkyl; —(CH$_2$)$_{0-6}$—$C_3$-$C_7$cycloalkyl; —O—(CH$_2$)$_{0-6}$-aryl; phenyl; —(CH$_2$)$_{1-6}$-het; —O—(CH$_2$)$_{1-6}$-het; —OR$_{11}'$; —C(O)—R$_{11}'$; —C(O)—N(R$_{11}'$)(R$_{12}'$); —N(R$_{11}'$)(R$_{12}'$); —S—R$_{11}'$; —S(O)—R$_{11}'$; —S(O)$_2$—R$_{11}'$; —S(O)$_2$—NR$_{11}'$R$_{12}'$; —NR$_{11}'$—S(O)$_2$—R$_{12}'$; wherein alkyl, cycloalkyl and aryl are unsubstituted or substituted; and $R_6''$, $R_7''$, $R_6'$ and $R_7'$ can be united to form a ring system;
$R_{11}'$ and $R_{12}'$ are independently H; $C_1$-$C_{10}$ alkyl; —(CH$_2$)$_{0-6}$—$C_3$-$C_7$cycloalkyl; —(CH$_2$)$_{0-6}$—(CH)$_{0-1}$(aryl)$_{1-2}$; —C(O)—$C_1$-$C_{10}$ alkyl; —C(O)—(CH$_2$)$_{1-6}$—$C_3$-$C_7$cycloalkyl; —C(O)—O—(CH$_2$)$_{0-6}$-aryl; —C(O)—(CH$_2$)$_{0-6}$—O-fluorenyl; —C(O)—NH—(CH$_2$)$_{0-6}$-aryl; —C(O)—(CH$_2$)$_{0-6}$-aryl; —C(O)—(CH$_2$)$_{1-6}$-het; —C(S)—$C_1$-$C_{10}$ alkyl; —C(S)—(CH$_2$)$_{1-6}$—$C_3$-$C_7$cycloalkyl; —C(S)—O—(CH$_2$)$_{0-6}$-aryl; —C(S)—(CH$_2$)$_{0-6}$—O-fluorenyl; —C(S)—NH—(CH$_2$)$_{0-6}$-aryl; —C(S)—(CH$_2$)$_{0-6}$-aryl; —C(S)—(CH$_2$)$_{1-6}$-het; wherein alkyl, cycloalkyl and aryl are unsubstituted or substituted; or $R_{11}'$ and $R_{12}'$ are a substituent that facilitates transport of the molecule across a cell membrane; or $R_{11}'$ and $R_{12}'$ together with the nitrogen atom form het; wherein the alkyl substituents of $R_{11}'$ and $R_{12}'$ may be unsubstituted or substituted by one or more substituents selected from $C_1$-$C_{10}$ alkyl, halogen, OH, —O—$C_1$-$C_6$alkyl, —S—$C_1$-$C_6$alkyl or —CF$_3$;
substituted cycloalkyl substituents of $R_{11}'$ and $R_{12}'$ are substituted by one or more substituents selected from a $C_1$-$C_{10}$ alkene; $C_1$-$C_6$alkyl; halogen; OH; —O—$C_1$-$C_6$alkyl; —S—$C_1$-$C_6$alkyl or —CF$_3$;
substituted phenyl or aryl of $R_{11}'$ and $R_{12}'$ are substituted by one or more substituents selected from halogen; hydroxy; $C_1$-$C_4$ alkyl; $C_1$-$C_4$ alkoxy; nitro; —CN; —O—C(O)—$C_1$-$C_4$alkyl and —C(O)—O—$C_1$-$C_4$-aryl; and wherein het is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S, which heterocyclic ring or fused ring system is unsubstituted or substituted on a carbon or nitrogen atom.

In one embodiment of Formula II, U—R$_5$ is

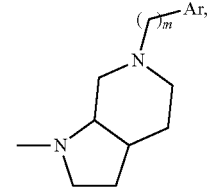

wherein m is 0, 1, 2, or 3, and Ar is substituted or unsubstituted aryl or het. In one embodiment, Ar is phenyl.
In another embodiment of Formula II:
$R_1'$ is H;
$R_2'$ is $C_1$-$C_4$ alkyl;
$R_3'$ is $C_1$-$C_4$ alkyl;
$R_4'$ is —$C_3$-$C_{10}$cycloalkyl;
$R_5'$ is H or $C_1$-$C_{10}$-alkyl;
and U is

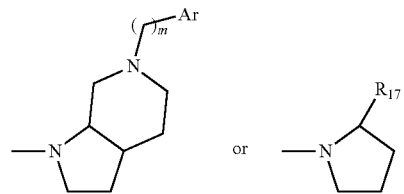

wherein m is 0, 1, 2, or 3, and Ar is substituted or unsubstituted aryl or het (e.g., Ar is substituted or unsubstituted phenyl or het); and
$R_{17}$ is Ar$_1$-D-Ar$_2$;
wherein Ar$_1$ and Ar$_2$ are substituted or unsubstituted aryl or het; and
D is —CO—; or —O—; or D is —N(Rx)- wherein Rx is H or $C_{1-7}$ alkyl.

The IAP inhibitors and methods of making them are disclosed in WO 2005/097791 and WO 2008/016893, both herein incorporated by reference in their entirety.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

As used herein, the term "cycloalkyl" refers to saturated or unsaturated monocyclic, bicyclic or tricyclic hydrocarbon groups of 3-12 carbon atoms, preferably 3-9, or 3-7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo [2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group.

"Alkoxy" refers to those alkyl groups, having from 1 to 10 carbon atoms, attached to the remainder of the molecule via an oxygen atom. Alkoxy groups with 1-8 carbon atoms are preferred. The alkyl portion of an alkoxy may be linear, cyclic, or branched, or a combination thereof. Examples of alkoxy groups include methoxy, ethoxy, isopropoxy, butoxy, cyclopentyloxy, and the like. An alkoxy group can also be represented by the following formula: —$OR^i$, where $R^i$ is the "alkyl portion" of an alkoxy group.

The term "heteroalkyl," by itself or in combination with another term, means, unless otherwise stated, a stable straight or branched chain, or combinations thereof, consisting of the stated number of carbon atoms and from one to five heteroatoms, more preferably from one to three heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

The term "alkylcarbonyl" refers to a group having the formula —C(O)—$R^{ii}$, wherein $R^{ii}$ is an alkyl group as defined above and wherein the total number of carbon atoms refers to the combined alkyl and carbonyl moieties. An "alkylcarbonyl" group can be attached to the remainder of the molecule via an alkyl group (i.e., -alkyl-C(O)—$R^{ii}$).

The term "alkoxycarbonyl" refers to a group having the formula —C(O)O—$R^{iii}$, wherein $R^{iii}$ is an alkyl group as defined above and wherein the total number of carbon atoms refers to the combined alkyl and carbonyl moieties. An "alkoxycarbonyl" group can be attached to the remainder of the molecule via an alkyl group (i.e., -alkyl-C(O)O—$R^{iii}$).

The term "heteroalkylcarbonyl" refers to a group having the formula —C(O)$R^{iv}$, wherein $R^{iv}$ is a heteroalkyl group as defined above and wherein the total number of carbon atoms refers to the combined alkyl and carbonyl moieties. A "heteroalkylcarbonyl" group can be attached to the remainder of the molecule via an alkyl or heteroalkyl group (i.e., -alkyl-C(O)O—$R^{iv}$ or -heteroalkyl-C(O)O—$R^{iv}$).

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" refers to a five-member to ten-member, fully saturated or partially unsaturated nonaromatic heterocylic groups containing at least one heteroatom such as O, S or N. The most frequent examples are piperidinyl, morpholinyl, piperazinyl, pyrrolidinyl or pirazinyl. Attachment of a heterocyclyl substituent can occur via a carbon atom or via a heteroatom.

Moreover, the alkyl, alkenyl, cycloalkyl, cycloalkenyl, alkoxy, aryl, heteroaryl, and heterocycle groups described above can be "unsubstituted" or "substituted." The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, (CR'R")$_{0-3}$NR'R" (e.g., —NH$_2$), (CR'R")$_{0-3}$CN (e.g., —CN), —NO$_2$, halogen (e.g., —F, —Cl, —Br, or —I), (CR'R")$_{0-3}$C(halogen)$_3$ (e.g., —CF$_3$), (CR'R")$_{0-3}$CH(halogen)$_2$, (CR'R")$_{0-3}$CH$_2$(halogen), (CR'R")$_{0-3}$CONR'R", (CR'R")$_{0-3}$(CNH)NR'R", (CR'R")$_{0-3}$S(O)$_{1-2}$NR'R", (CR'R")$_{0-3}$CHO, (CR'R")$_{0-3}$O(CR'R")$_{0-3}$H, (CR'R")$_{0-3}$S(O)$_{0-3}$R' (e.g., —SO$_3$H, —OSO$_3$H), (CR'R")$_{0-3}$O(CR'R")$_{0-3}$H (e.g., —CH$_2$OCH$_3$ and —OCH$_3$), (CR'R")$_{0-3}$S(CR'R")$_{0-3}$H (e.g., —SH and —SCH$_3$), (CR'R")$_{0-3}$OH (e.g., —OH), (CR'R")$_{0-3}$COR', (CR'R")$_{0-3}$(substituted or unsubstituted phenyl), (CR'R")$_{0-3}$(C$_3$-C$_8$ cycloalkyl), (CR'R")$_{0-3}$CO$_2$R' (e.g., —CO$_2$H), or (CR'R")$_{0-3}$OR' group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

In a particular embodiment of the invention, the term "amine" or "amino" refers to substituents of the formulas $N(R^8)R^9$, $CH_2N(R^8)R^9$ and $CH(CH_3)N(R^8)R^9$, wherein $R^8$ and $R^9$ are each, independently, selected from the group consisting of H and $(C_1$-$C_4$-alkyl)$_{0-1}$G, wherein G is selected from the group consisting of COOH, H, PO$_3$H, SO$_3$H, Br, Cl, F, O—$C_{1-4}$-alkyl, S—$C_{1-4}$-alkyl, aryl, C(O)OC$_1$-$C_6$-alkyl, C(O)C$_1$-$C_4$-alkyl-COOH, C(O)C$_1$-$C_4$-alkyl and C(O)-aryl.

It will be noted that the structures of some of the compounds of this invention include asymmetric carbon atoms. It is to be understood accordingly that the isomers arising from such asymmetry (e.g., all enantiomers and diastereomers) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein can be obtained through art recognized synthesis strategies.

In a preferred embodiment, the IAP inhibitor is LBW 242 (N-[1-cyclohexyl-2-oxo-2-(6-phenethyl-octahydro-pyrrolo [2,3-c]pyridin-1-yl)-ethyl]-2-methylamino-propionamide):

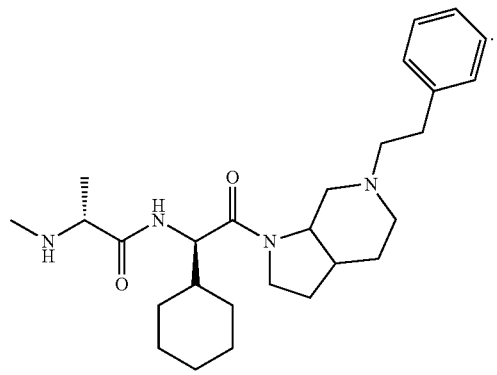 [SMILES: CN[C@H](C)C(=O)N[C@@H](C(=O)N1CCC2CCN(CCc3ccccc3)CC21)C1CCCCC1]

The following represent compounds which can be used as IAP inhibitors in the present application:

| Ex | Name | +MS ESI (M + H)$^+$ |
|---|---|---|
| 1 | (S) - N-((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide | |
| 2 | (S) - N-[(S)-Cyclohexyl-(ethyl-{(S)-1-[5-(4-fluoro-benzoyl)-pyridin-3-yl]-propyl}-carbamoyl)-methyl]-2-methylamino-propionamide | |
| 3 | (S) - N-((S)-1-Cyclohexyl-2-{(S)-2-[5-(4-fluoro-phenoxy)-pyridin-3-yl]-pyrrolidin-1-yl}-2-oxo-ethyl)-2-methylamino-propionamide | |

-continued

| Ex | Name | +MS ESI (M + H)+ |
|---|---|---|
| 4 | (S) - N-((S)-1-Cyclohexyl-2-{(S)-2-[4-(4-fluoro-phenoxy)-pyridin-2-yl]-pyrrolidin-1-yl}-2-oxo-ethyl)-2-methylamino-propionamide | |
| 5 | (S) - N-[(S)-Cyclohexyl-2-((S)-2-{5-fluoro-2-[(4-fluoro-phenyl)-methyl-amino]-pyridin-4-yl}-pyrrolidin-1-yl)-2-oxo-ethyl]-2-methylamino-propionamide | |
| 6 | (S) - N-((S)-1-Cyclohexyl-2-{(S)-2-[4-(4-fluoro-benzoyl)-5-methyl-thiazo-1-2-yl]-pyrrolidin-1-yl}-2-oxo-ethy-1)-2-methylamino-propionamide | 515 |
| 7 | (S) - N-{(S)-2-[(S)-2-(4-Benzoyl-5-methyl-oxazol-2-yl)-pyrrolidin-1-yl]-1-cyclohexyl-2-oxo-ethyl}-2-methylamino-propionamide | 481 |
| 8 | (S) - N-((S)-1-Cyclohexyl-2-{(S)-2-[4-(4-fluoro-benzoyl)-5-methyl-oxazol-2-yl]-pyrrolidin-1-yl}-2-oxo-ethyl)-2-methylamino-propionamide | 499 |
| 9 | (S) - N-((S)-1-Cyclohexyl-2-{(S)-2-[4-(4-fluoro-benzoyl)-5-methyl-thiazol-2-yl]-pyrrolidin-1-yl}-2-oxo-ethyl)-2-methylamino-propionamide | 487 |
| 10 | (S) - N-{(S)-2-[(S)-2-(4-Benzoyl-oxazol-2-yl)-pyrrolidin-1-yl]-1-cyclohexyl-2-oxo-ethyl}-2-methylamino-propionamide | 485 |
| 11 | (S) - N-((S)-1-Cyclohexyl-2-{(S)-2-[4-(2,4-difluoro-benzoyl)-thiazol-2-yl]-pyrrolidin-1-yl}-2-oxo-ethyl)-2-methylamino-propionamide | 519 |
| 12 | (S) - N-((S)-1-Cyclohexyl-2-{(S)-2-[4-(1H-indole-2-carbonyl)-thiazol-2-yl]-pyrrolidin-1-yl}-2-oxo-ethyl)-2-methylamino-propionamide | 522 |
| 13 | (S) - N-((S)-1-Cyclohexyl-2-{(S)-2-[2-(4-fluoro-phenoxy)-pyridin-4-yl]-pyrrolidin-1-yl}-2-oxo-ethyl)-2-methylamino-propionamide | 483.27 |
| 14 | (S) - N-[(S)-1-((S)-2-{2-[(4-Fluoro-phenyl)-methyl-amino]-pyridin-4-yl}-pyrrolidine-1-carbonyl)-2-methyl-propyl]-2-methylamino-propionamide | 456.27 |
| 15 | (S) - N-((S)-1-Cyclohexyl-2-{(S)-2-[2-(4-fluoro-benzoyl)-pyridin-4-yl]-pyrrolidin-1-yl}-2-oxo-ethyl)-2-methylamino-propionamide | 495.27 |
| 16 | (S) - N-((S)-1-Cyclohexyl-2-{(S)-2-[2-(5-fluoro-pyridin-2-ylamino)-pyridin-4-yl]-pyrrolidin-1-yl}-2-oxo-ethyl)-2-methylamino-propionamide | 483.28 |
| 17 | (S) - N-[(S)-1-Cyclohexyl-2-((S)-2-{3-fluoro-2-[(4-fluoro-phenyl)-methyl-amino]-pyridin-4-yl}-pyrrolidin-1-yl)-2-oxo-ethyl]-2-methylamino-propionamide | 514.29 |
| 18 | (S) - N-((S)-1-Cyclohexyl-2-{(S)-2-[3-fluoro-2-(4-fluoro-benzoyl)-pyridin-4-yl]-pyrrolidin-1-yl}-2-oxo-ethyl)-2-methylamino-propionamide | 513.26 |
| 19 | (S) - N-[(S)-2-((S)-2-{2-Amino-6-[N-(4-fluoro-phenyl)-hydrazino]-pyridin-4-yl}-pyrrolidin-1-yl)-1-cyclohexyl-2-oxo-ethyl]-2-methylamino-propionamide | 512.31 |
| 20 | (S) - N-{(S)-1-Cyclohexyl-2-oxo-2-[(S)-2-(4-phenoxy-pyridin-2-yl)-pyrrolidin-1-yl]-ethyl}-2-methylamino-propionamide | 465.3 |
| 21 | (S) - N-((S)-1-Cyclohexyl-2-{(S)-2-[6-(4-fluoro-phenoxy)-2-methyl-pyrimidin-4-yl]-pyrrolidin-1-yl}-2-oxo-ethyl)-2-methylamino-propionamide | 498.3 |
| 22 | (S) - N-((S)-1-Cyclohexyl-2-{(S)-2-[4-(4-fluoro-benzoyl)-pyridin-2-yl]-pyrrolidin-1-yl}-2-oxo-ethyl)-2-methylamino-propionamide | 495.3 |
| 23 | (S) - N-((S)-1-Cyclohexyl-2-{(S)-2-[6-(4-fluoro-benzoyl)-2-methyl-pyrimidin-4-yl]-pyrrolidin-1-yl}-2-oxo-ethyl)-2-methylamino-propionamide | 510.3 |
| 24 | (S) - N-[(S)-1-Cyclohexyl-2-((S)-2-{5-[(4-fluoro-phenyl)-methyl-amino]-pyridin-3-yl}-pyrrolidin-1-yl)-2-oxo-ethyl]-2-methylamino-propionamide | 496.3 |
| 25 | (S) - N-[(S)-1-Cyclohexyl-2-((S)-2-{4-[(4-fluoro-phenyl)-methyl-amino]-pyridin-2-yl}-pyrrolidin-1-yl)-2-oxo-ethyl]-2-methylamino-propionamide | 496.3 |
| 26 | (S) - N-[(S)-1-Cyclohexyl-2-((S)-2-{6-[(4-fluoro-phenyl)-methyl-amino]-2-methyl-pyrimidin-4-yl}-pyrrolidin-1-yl)-2-oxo-ethyl]-2-methylamino-propionamide | 511.3 |
| 27 | (S) - N-((S)-1-{(S)-2-[6-(4-Fluoro-benzoyl)-2-methyl-pyrimidin-4-yl]-pyrrolidine-1-carbonyl}-2-methyl-propyl)-2-methylamino-propionamide | 458.2 |
| 28 | (S) - N-((S)-1-{(S)-2-[6-(4-Fluoro-benzoyl)-2-methyl-pyrimidin-4-yl]-pyrrolidine-1-carbonyl}-2-methyl-propyl)-2-methylamino-propionamide | 470.2 |
| 29 | (S) - N-[(S)-1-((S)-2-{6-[(4-Fluoro-phenyl)-methyl-amino]-2-methyl-pyrimidin-4-yl}-pyrrolidine-1-carbonyl)-2-methyl-propyl]-2-methylamino-propionamide | 471.3 |
| 30 | (S) - N-((S)-1-Cyclohexyl-2-{(S)-2-[6-(4-fluoro-phenylamino)-2-methyl-pyrimidin-4-yl]-pyrrolidin-1-yl}-2-oxo-ethyl)-2-methylamino-propionamide | 497.3 |

-continued

| Ex | Name | +MS ESI (M + H)+ |
|---|---|---|
| 31 | (S) - N-((S)-1-{(S)-2-[6-(4-Fluoro-phenylamino)-2-methyl-pyrimidin-4-yl]-pyrrolidine-1-carbonyl}-2-methyl-propyl)-2-methylamino-propionamide | 457.3 |

II. Immunomodulatory Properties of IAP Inhibitors

To bring about an immune response in a subject, it is common to administer an immune stimulus, an immunogen or an antigen in combination with an immune adjuvant. An adjuvant is a substance that enhances an immune response to an immune stimulus, immunogen or antigen. According to the present invention, IAP inhibitors, including Smac mimetics, are potent immune adjuvants. IAP inhibitors are capable of enhancing physiologically relevant activation signals in diverse lineages of immune cells. IAP inhibitors do not alter the function of resting immune cells, but enhance immune cell activation in the context of stimulation. Immune cell activation is evidenced by, e.g., increased expansion, cytokine production, and alterations in expression of cell surface markers. Cell types that respond to IAP inhibitors include, but are not limited to, dentritic cells, B cells, T cells (e.g., CD4+ T cells, CD8+ T cells and NKT cells), NK cells, and macrophages, plasma cells, and hybridomas.

The term "subject" as used herein is intended to include animals, which are capable of suffering from or afflicted with a disease or disorder, such as cancer, or is need of having its immune response enhanced. Examples of subjects include mammals, e.g., humans, mice, rabbits, rats, dogs, cows, horses, pigs, sheep, goats, cats, donkeys, and transgenic non-human animals. In certain embodiments, the subject is a human, e.g., a human suffering from, at risk of suffering from, or potentially capable of suffering from a disease or disorder, such as cancer, or in need of having his or her immune response enhanced.

The scope of immune signals enhanced by IAP inhibitors exceeds that of currently known adjuvants. In addition, IAP inhibitors are able to stimulate more broadly diverse lineages of immune cells than currently known adjuvants. These properties position IAP inhibitors as ideal agents for the promotion of immunity. By amplifying weak immune signals, IAP inhibitors can function as vaccine adjuvants, and can additionally be used to enhance immunity to chronic infections or tumors.

IAP inhibitors are also useful in certain autoimmune diseases where immune stimulation speeds disease resolution. In a particular embodiment, the IAP inhibitor is a compound of Formula I or Formula II, such LBW 242 (N-[1-cyclohexyl-2-oxo-2-(6-phenethyl-octahydro-pyrrolo [2,3-c]pyridin-1-yl)-ethyl]-2-methylamino-propionamide). Additional therapeutic applications of IAP inhibitors are described in greater detail below.

III. Therapeutic Compositions and Methods (A) Adjuvants and Vaccines

The immunomodulatory properties of IAP inhibitors make IAP inhibitors ideal adjuvants. Accordingly, the present invention features an immune adjuvant comprising an IAP inhibitor. Such immune adjuvants may be administered to a subject alone or in combination with an antigen or immunogen. The antigen or immunogen may be a vaccine or a component of a vaccine. The invention further features pharmaceutical compositions containing an antigen and an IAP inhibitor. In addition, the invention features vaccines containing an antigen and an IAP inhibitor.

The quantity of an IAP inhibitor provided in such pharmaceutical compositions and/or vaccines, or administered in combination with an antigen is typically an immune enhancing amount. An "immune enhancing amount" of an IAP inhibitor as used herein refers to any quantity of an IAP inhibitor capable of stimulating or enhancing any indicator of immune response. In exemplary embodiments, the immune enhancing amount of an IAP inhibitor is therapeutically effective in treating or preventing a disease. Enhancement of an immune response, as used herein, refers to enhancing an immune response relative to the level of immune response that would occur in the absence of an IAP inhibitor of the invention.

The quantity of antigen provided in such pharmaceutical compositions and/or vaccines, or administered in combination with an IAP inhibitor, is preferably an immunogenic quantity. The antigen may be immunogenic when administered alone, or may be immunogenic only when administered in combination with an adjuvant, e.g., an IAP inhibitor. The amount of antigen is typically an amount which induces an immune response in a subject without significant adverse side effects. The quantity of an antigen which is immunogenic when administered alone may be reduced when administered in combination with an immune adjuvant of the invention, or when administered as a component of a pharmaceutical composition or vaccine of the invention. Reducing the quantity of antigen required to stimulate an immune response in a subject is desirable as it reduces the probability of unwanted side effects associated with some antigens currently in use.

As used herein, the term "antigen" refers to any molecule or composition capable of stimulating or enhancing any indicator of immune response. Indicators of an immune response include, but are not limited to, any of the following immune activities: cytokine production, antibody production, immune cell activation, immune cell expansion, immune cell proliferation, immune cell mediated cytotoxicity, and alterations in expression of immune cell surface markers. The term "antigen" is used interchangeably with the term "immunogen." An "immunogenic quantity" of an antigen as used herein refers to any quantity of an antigen capable of stimulating or enhancing any indicator of immune response.

Stimulation or enhancement of an immune response may be determined using any suitable method known in the art, including but not limited to detecting changes in cytokine production, antibody production, immune cell activation, immune cell expansion, immune cell mediated cytotoxicity, and alterations in expression of immune cell surface markers. Immune cells capable of an immune response include, but are not limited to, dendritic cells, B cells, T cells (e.g., CD4+ T cells, CD8+ T cells and NKT cells), NK cells, macrophages, plasma cells, and hybridomas.

The term "vaccine," as used herein, broadly refers to any preparation of antigenic material used to induce immunity.

(B) Methods of Enhancing an Immune Response

The present invention provides a method of enhancing an immune response in a subject by administering to the subject an IAP inhibitor. Such an immune response is typically mediated by one or more immune cell types, including, but not limited to, dendritic cells, B cells, T cells (e.g., CD4+ T cells, CD8+ T cells and NKT cells), NK cells, macrophages, plasma cells, and hybridomas. This method may involve selecting a subject in need of an enhanced immune response. A subject selected for this method of enhancing an immune response may be a subject exhibiting a low level of immune response to an antigen, e.g., a tumor antigen or a viral antigen.

The present invention further provides a method of enhancing an immune response of a subject to an antigen by administering to the subject an antigen in combination with an IAP inhibitor. In a particular embodiment, the IAP inhibitor is a compound of Formula I or Formula II, such as LBW 242 (N-[1-cyclohexyl-2-oxo-2-(6-phenethyl-octahydro-pyrrolo[2,3-c]pyridin-1-yl)-ethyl]-2-methylamino-propionamide). The antigen may be immunogenic when administered alone, or may be immunogenic only when administered in combination with an adjuvant, e.g., an IAP inhibitor. Such an immune response is typically mediated by one or more immune cell types, including, but not limited to, dendritic cells, B cells, T cells (e.g., CD4+ T cells, CD8+ T cells and NKT cells), NK cells, macrophages, plasma cells, and hybridomas. The antigen and the IAP inhibitor may be administered in separate compositions, or may be components of a single composition. In the event that the antigen and the IAP inhibitor are administered as separate compositions, the compositions may be administered either simultaneously or sequentially. The antigen and/or the IAP inhibitor may be administered as a single dose, or as multiple doses.

Antigens suitable for use in practice of the invention include, but are not limited to, mammalian antigens, plant antigens, tumor antigens, microbial antigens, viral antigens, and fungal antigens. These antigens may be isolated or otherwise purified, or may be present within a mixture of other compounds. Suitable antigens include, for example, mammalian proteins, plant proteins, tumor proteins, microbial proteins, viral proteins, and fungal proteins. Suitable antigens also include live, attenuated, or killed cells or cell fragments, including tumor cells, microbial cells, cells infected with a virus, and fungal cells. Additional suitable antigens include nucleic acid molecules (e.g., DNA, RNA, etc.) capable of inducing an immune response.

(C) Methods of Treating Cancer

The term "treated," "treating" or "treatment" includes the diminishment or alleviation of at least one symptom associated with the condition being treated. For example, treatment can be diminishment of one or several symptoms of a disorder or complete eradication of a disorder, such as cancer.

The immune system response to cancer cells and tumor antigens is generally low, making vaccination a problematic approach in treating cancer. The potency and scope of immune signals enhanced by IAP inhibitors (e.g., compounds of Formula I or Formula II) make IAP inhibitors (and adjuvants, compositions, and vaccines comprising the same) particularly useful in improving the immune response to cancer. Cancer vaccines containing or coadministered with IAP inhibitors are therefore advantageous in treating and/or preventing cancer. Accordingly, the invention provides methods of treating or reducing the symptoms of cancer in a subject, by administering to a subject having cancer a therapeutically effective amount of an IAP inhibitor and an antigen, where the IAP inhibitor and the antigen enhance the immune response of the subject to the cancer such that the cancer is treated. The invention further provides methods of preventing cancer in a subject, by administering to a subject at risk of developing a cancer a therapeutically effective amount of an IAP inhibitor and an antigen, such that the immune response of the subject to the antigen is enhanced, and such that the development of cancer in the subject is prevented. The antigen may be immunogenic when administered alone, or may be immunogenic only when administered in combination with an adjuvant, e.g., an IAP inhibitor. Such an immune response is typically mediated by one or more immune cell types, including, but not limited to, dendritic cells, B cells, T cells (e.g., CD4+ T cells, CD8+ T cells and NKT cells), NK cells, macrophages, plasma cells, and hybridomas. The antigen and the IAP inhibitor may be administered in separate compositions, or may be components of a single composition. In the event that the antigen and the IAP inhibitor are administered as separate compositions, the compositions may be administered either simultaneously or sequentially. The antigen and/or the IAP inhibitor may be administered as a single dose, or as multiple doses.

Antigens suitable for use in the foregoing methods of treating or reducing the symptoms of cancer in a subject include any antigen associated with the subject's cancer. Such an antigen may be present in cancer cells and absent from non-cancerous cells. Alternatively, such an antigen may be present at elevated levels in cancer cells relative to non-cancerous cells. Differentially expressed antigens may be identified using any suitable technique known in the art, including, but not limited to, Northern blot, Western blot, quantitative RT-PCR, in situ hybridization, oligonucleotide microarray analysis, antibody array analysis, differential display, subtractive hybridization, and serial analysis of gene expression (SAGE). In an exemplary embodiment, the antigen is a cell-surface antigen. The antigen may be an antigen known to be differentially expressed in cancer cells with respect to non-cancerous cells. Alternatively, the antigen may be identified by comparison of a cancer cell or cell sample obtained from the subject having cancer with a normal cell or cell sample obtained from a subject. The antigens may be isolated or otherwise purified, or may be present as components of a mixture.

Suitable antigens also include live, killed, or attenuated cancer cells or cancer cell fragments. Cancer cells may be irradiated or otherwise treated prior to use as an antigen such that they are proliferation incompetent. Cells may also be disrupted, sheared, sonicated, or lysed prior to use as an antigen. In a preferred embodiment, the cancer cells used as an antigen are autologous cells obtained from a subject to whom the antigen will be administered according to the methods described herein. In another embodiment, the cancer cells used as an antigen are allogeneic cells.

Antigens suitable for use in the foregoing methods of preventing cancer in a subject include any antigen known to be frequently present in a particular type of cancer cell and absent from non-cancerous cells, or any antigen known to be frequently present at elevated levels in cancer cells relative to non-cancerous cells. Such antigens include, but are not limited to, mucin-1 (MUC-1), prostate specific antigen (PSA), carcinoembryonic antigen (CEA), prostatic acid phosphatase (PAP), and members of the melanoma antigen gene family (MAGE). Infection by certain viruses is known to increase a subject's likelihood of developing cancer. Antigens associated with such viruses are also suitable for use in the foregoing methods of preventing cancer. Such antigens can be isolated or otherwise purified, or may include all or a portion of live, killed, or attenuated viral particles. Viruses associated with increasing the susceptibility of a subject to cancer include, but are not limited to, human papillomavirus (HPV), hepatitis B, hepatitis C, herpesvirus, Epstein-Barr virus, human T-cell lymphotrophic virus, and HIV-1. Enhancing the immune response of a subject to the foregoing antigens enables the subject to resist subsequent challenge with a virus or cancer cell containing the antigen, and accordingly prevents the subject from developing a cancer.

Methods suitable for assessing the enhancement of an immune response, including an immune response to a cancer, are known in the art. Such methods include, but are not limited to, antibody titer, measurement of cytokine production, limiting dilution assay, ELISA (to measure cytokine production), tetramer assays, immunophenotyping using, e.g., the FastImmune™ Assay (BD Biosciences, Franklin Lakes, N.J.), and enzyme-linked immunosorbent spot (ELISPOT) assays. Clinical endpoints useful for measuring response to cancer treatment are likewise known in the art and include, but are not limited to, reduction in tumor volume, overall survival, disease free survival and time to disease progression.

Because the IAP inhibitors of the invention broadly enhance the immune response, the foregoing methods are useful in treating a broad spectrum of tumors, including all solid tumors and hematological malignancies. Examples of such tumors include but are not limited to leukemias, lymphomas, myelomas, carcinomas, metastatic carcinomas, sarcomas, adenomas, nervous system cancers and geritourinary cancers. In exemplary embodiments, the foregoing methods are useful in treating adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

Also provided are methods of treating cancer ex vivo. According to these methods, a population of immune cells is isolated from a subject having cancer, and the immune cells are stimulated with an antigen and a therapeutically effective amount of an IAP inhibitor, such that the immune cells are activated against the antigen. The immune cells are then returned to the subject. Such immune cells then enhance the immune response of a subject against the subject's cancer. Antigens suitable for the methods of treating, preventing or reducing the symptoms of cancer in a subject as described above are likewise suitable for methods of treating cancer ex vivo. Several experimental treatment protocols known in the art involve ex vivo activation and expansion of antigen specific T cells and adoptive transfer of these cells into recipients in order to provide antigen-specific T cells against a recipient's tumor (see, for example, Greenberg, R. and Riddell, S. (1999) *Science* 285:546-551). These methods may also be used to activate T cell responses to infectious agents, including infectious agents which increase a subject's likelihood of developing cancer, as described herein. Ex vivo activation in the presence of an IAP inhibitor of the invention may increase the frequency and activity of adoptively transferred T cells. Use of IAP inhibitors to enhance maturation of dentritic cells during production of a dendritic cell vaccine is also contemplated.

(D) Methods of Treating or Preventing Infectious Diseases

The potency and scope of immune signals enhanced by IAP inhibitors (e.g., compounds of Formula I or Formula II) make IAP inhibitors (and adjuvants, compositions, and vaccines comprising the same) particularly useful in enhancing the immune response of a subject to an infectious agent. IAP inhibitors can be incorporated in or administered in combination with vaccines, improving the immunogenicity of the vaccine antigen. Vaccines containing or administered in combination with IAP inhibitors are therefore useful in preventing infection caused by an infectious agent, and are further useful in treating such infections if administered after infection has occurred. Accordingly, the invention features methods of treating an infection caused by an infectious agent, by administering to a subject a therapeutically effective amount of an IAP inhibitor and an antigen, where the IAP inhibitor and the antigen enhance the immune response of the subject to the infectious agent, such that the infection is treated. The invention likewise features methods of preventing an infection caused by an infectious agent, by administering to a subject a therapeutically effective amount of an IAP inhibitor and an antigen, where the IAP inhibitor and the antigen enhance the immune response of the subject to the infectious agent, such that infection is prevented. Such an immune response is typically mediated by one or more immune cell types, including, but not limited to, dendritic cells, B cells, T cells (e.g., CD4+ T cells, CD8+ T cells and NKT cells), NK cells, macrophages, and plasma cells. The antigen and the IAP inhibitor may be administered in separate compositions, or may be components of a single composition. In the event that the antigen and the IAP inhibitor are administered as separate compositions, the compositions may be administered either simultaneously or sequentially. The antigen and/or the IAP inhibitor may be administered as a single dose, or as multiple doses.

Infectious diseases that may be treated or prevented using the foregoing methods include, but are not limited to, infectious diseases caused by infectious agents such as bacteria, viruses, protozoa, fungi and parasites. Suitable antigens include any antigen associated with an infectious agent. The antigens may be isolated or otherwise purified, or may be present as components of a mixture. Suitable antigens also include whole, live, killed, or attenuated infectious agent particles, e.g., bacterial cells, viruses, protozoa, fungi, or parasites, or fragments of the same. These infectious agents may be irradiated or otherwise treated prior to use as an antigen such that they are proliferation incompetent, replication incompetent, or otherwise incapable of producing an active infection. Infectious agents may also be disrupted, sheared, sonicated, or lysed prior to use as an antigen.

Methods suitable for assessing the enhancement of an immune response to an antigen are known in the art and include, for example, antibody titer, limiting dilution assay, ELISA (to measure cytokine production), tetramer assays, immunophenotyping using, e.g., the FastImmune™ Assay (BD Biosciences, Franklin Lakes, N.J.), and enzyme-linked immunosorbent spot (ELISPOT) assays. Clinical endpoints useful for measuring response to treatment of an infectious agent are likewise known in the art and include, but are not limited to, reduction in bacterial titer, reduction in viral titer, and amelioration of symptoms associated with an infectious disease.

(E) Methods of Enhancing Immune Cell Proliferation and/or Cytokine Secretion

Immune activation induces proliferation and expansion of immune cell lineages. By enhancing immune cell activation, IAP inhibitors of the invention (e.g., compounds of Formula I or Formula II) increase proliferation and expansion of a diverse range of immune cells, including, but not limited to, dendritic cells, B cells, T cells (e.g., CD4+ T cells, CD8+ T cells and NKT cells), NK cells, and macrophages. Accordingly, the invention features methods of potentiating immune cell proliferation by contacting a cell population that includes an immune cell with an IAP inhibitor. In a preferred embodiment, cells are contacted with additional immune activation stimuli in combination with an IAP inhibitor to enhance immune cell proliferation. In this embodiment, cells contacted with an IAP inhibitor and additional immune activation stimuli demonstrate greater expansion than they otherwise would when contacted with immune activation stimuli in the absence of an IAP inhibitor. Stimuli that initiate immune activation are known in the art and include, but are not limited to, α-galcer, anti-CD3, anti-CD28, anti-IgM, and anti-CD40. Additional immune stimuli are described in, for example, Advanced Methods in Cellular Immunology, Fernandez-Botran et al., CRC; Spi edition (May 26, 2000).

Immune activation also induces expression and secretion of cytokines in immune cells. By enhancing immune cell activation, IAP inhibitors of the invention increase production and secretion of cytokines in immune cells. Such cytokines include, but are not limited to, IFN-γ, IFN-α, IL-2, IL-4, IL-6, IL-8, IL-10, IL-12, TNFα, TNFβ, TGFβ, and GM-CSF. Accordingly, the invention features methods of potentiating cytokine production by contacting a cell population that includes an immune cell with an IAP inhibitor. In a preferred embodiment, cells are contacted with additional immune activation stimuli in combination with an IAP inhibitor to enhance cytokine production. In this embodiment, cells contacted with an IAP inhibitor and additional immune activation stimuli demonstrate greater cytokine production than they otherwise would when contacted with immune activation stimuli in the absence of an IAP inhibitor. Stimuli that initiate immune activation are known in the art and include, but are not limited to, α-galcer, anti-CD3, anti-CD28, anti-IgM, and anti-CD40. Additional immune stimuli are described in, for example, Advanced Methods in Cellular Immunology, Fernandez-Botran et al., CRC; Spi edition (May 26, 2000), as noted above.

(F) Methods of Improving Antibody Production

Many commercially important antigens are poorly immunogenic, and obtaining antibodies recognizing such antigens has traditionally been difficult. The ability of IAP inhibitors of the invention to function as potent immune adjuvants makes the IAP inhibitors particularly suitable for enhancing the efficiency of polyclonal and/or monoclonal antibody production. IAP inhibitors are especially useful in producing antibodies recognizing poorly immunogenic antigens. Accordingly, the invention features methods of enhancing antibody production by immunizing a mammal with an antigen and an IAP inhibitor. Methods known in the art useful for isolating monoclonal and/or polyclonal antibodies following immunization are suitable for practicing the invention. A greater number of hybridomas recognizing the antigen are produced when monoclonal antibodies are isolated from animals immunized with an antigen and an IAP inhibitor than would otherwise be produced when monoclonal antibodies are isolated from animals immunized with antigen alone. Likewise, the reactivity of polyclonal antibodies isolated from antiserum of animals immunized with an antigen and an IAP inhibitor is greater than that of polyclonal antibodies isolated from antiserum of animals immunized with antigen alone. Accordingly, use of an IAP inhibitor to enhance monoclonal and/or polyclonal antibody production can improve the efficiency of antibody production in commercial sectors. Following isolation of a hybridoma that produces an antibody of interest, antibody production can be enhanced by contacting the hybridoma with an IAP inhibitor. Accordingly, IAP inhibitors are useful for augmenting monoclonal antibody production from hybridomas. In a particular embodiment, the IAP inhibitor is a compound of Formula I or Formula II, such as LBW 242 (N-[1-cyclohexyl-2-oxo-2-(6-phenethyl-octahydro-pyrrolo [2,3-c]pyridin-1-yl)-ethyl]-2-methylamino-propionamide).

(G) Formulations and Methods of Administration

Pharmaceutical Compositions

The present invention also provides pharmaceutical compositions. Such compositions comprise a therapeutically (or prophylactically) effective amount of an IAP inhibitor, and a pharmaceutically acceptable carrier or excipient. Suitable pharmaceutically acceptable carriers include, but are not limited to, saline, buffered saline, dextrose, water, glycerol, ethanol, and combinations thereof. The carrier and composition can be sterile. The formulation should suit the mode of administration.

The phrase "pharmaceutically acceptable carrier" is art recognized and includes a pharmaceutically acceptable material, composition or vehicle, suitable for administering compounds of the present invention to mammals. The carriers may include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the subject. Some examples of materials which can serve as pharmaceutically acceptable carriers include: sugars, such as lactose, glucose, dextrose and sucrose; starches, such as corn starch and potato starch; cellulose, and its derivatives, such as sodium carboxymethyl cellulose, ethyl cellulose, methylcellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, castor oil, tetraglycol, and soybean oil; glycols, such as propylene glycol; polyols, such as glycerin, sorbitol, mannitol and polyethylene glycol; esters, such as ethyl oleate, esters of polyethylene glycol and ethyl laurate; agar; buffering agents, such as magnesium hydroxide, sodium hydroxide, potassium hydroxide, carbonates, triethylanolamine, acetates, lactates, potassium citrate and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, t-tocopherol and derivatives such as vitamin E tocopherol, and the like; and metal chelating agents, such as citric acid, ethylenediamine tetraacetic acid (EDTA), sorbitol, tartaric acid, phosphoric acid, sodium citrate and the like.

Suitable pharmaceutically acceptable carriers include but are not limited to water, salt solutions (e.g., NaCl), alcohols, gum arabic, vegetable oils, benzyl alcohols, polyethylene glycols, gelatin, carbohydrates such as lactose, amylose or starch, cyclodextrin, magnesium stearate, talc, silicic acid, viscous paraffin, perfume oil, fatty acid esters, hydroxymethylcellulose, polyvinyl pyrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. The pharmaceutically acceptable carriers can also include a tonicity-adjusting agent such as dextrose, glycerine, mannitol and sodium chloride.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrolidone, sodium saccharine, cellulose, magnesium carbonate, etc.

The composition can be formulated in accordance with the routine procedures as a pharmaceutical composition adapted for oral, subcutaneous, or intravenous administration to human beings. Typically, compositions for subcutaneous or intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients can be mixed prior to administration.

Formulations of the present invention include those suitable for subcutaneous, intravenous, oral, nasal, topical, mucous membrane, transdermal, buccal, sublingual, rectal, vaginal and/or parenteral administration. The formulations can conveniently be presented in unit dosage form and can be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention can also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

The tablets, and other solid dosage forms of the pharmaceutical compositions of the present invention, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions that can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms can contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration can be presented as a suppository, which can be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound can be mixed under sterile conditions with a pharmaceutically acceptable carrier, and with any preservatives, buffers, or propellants that can be required.

The ointments, pastes, creams and gels can contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers that can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents that delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

Kits

Advantageously, the present invention also provides kits for use by a consumer for treating or preventing disease. The kits comprise a) a pharmaceutical composition comprising an IAP inhibitor (e.g., a compound of the Formula I or Formula II, e.g., LBW 242) and a pharmaceutically acceptable carrier, vehicle or diluent; and, optionally, b) instructions describing a method of using the pharmaceutical composition for treating or preventing a specific disease. In exemplary embodiments, the instructions describe a method of using the pharmaceutical composition for enhancing an immune response. In another exemplary embodiment, the instructions describe a method of using the pharmaceutical composition for treating or preventing cancer. In another exemplary embodiment, the instructions describe a method of enhancing an immune activity of an immune cell. Kits of the invention may further contain an antigen to be administered or otherwise used in conjunction with the pharmaceutical composition.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

This invention is further illustrated by the following examples, which should not be construed as limiting.

EXAMPLES

Example 1: NKT Cell Development in Fetal Thymic Organ Culture (FTOC) is Blocked by Treatment with IAP Inhibitors In order to investigate the role of IAP family members in NKT cell development, pharmacologic mimetics of the endogenous IAP inhibitor second mitochondrial activator of apoptosis (SMAC) were obtained. Three chemically distinct inhibitors were used for most experiments. One such inhibitor, LBW-242, is a potent inhibitor of IAP family members which binds to the XIAP BIR domain at submicromolar concentrations ($IC_{50}$=280 nM). LBW-242 was used for most experimental replications.

Figure 1B:
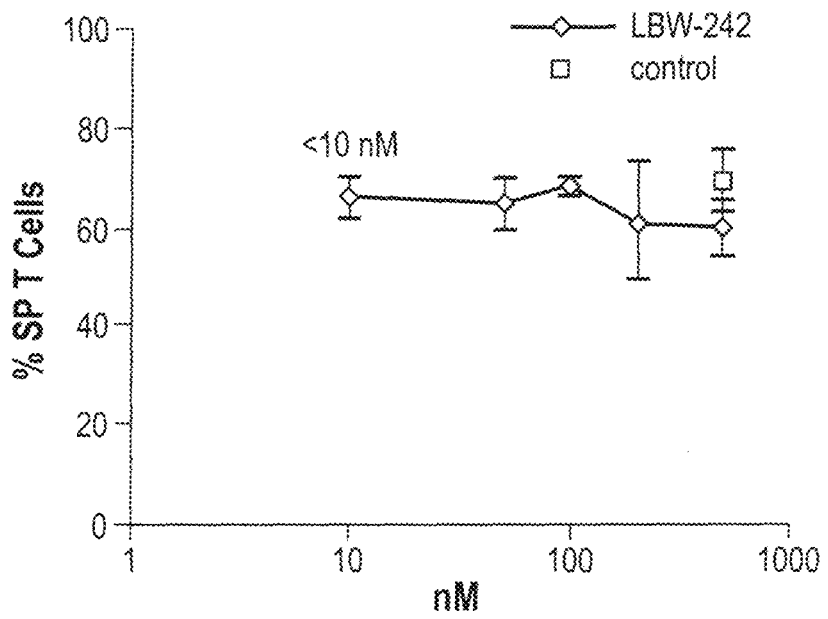
FIG. 1B depicts data, which indicates that NKT cell development in fetal thymic organ culture (FTOC) is blocked by treatment with IAP inhibitors, namely single positive thymocyte development at day 14 as a function of LBW-242 concentration.
Figure 1C:
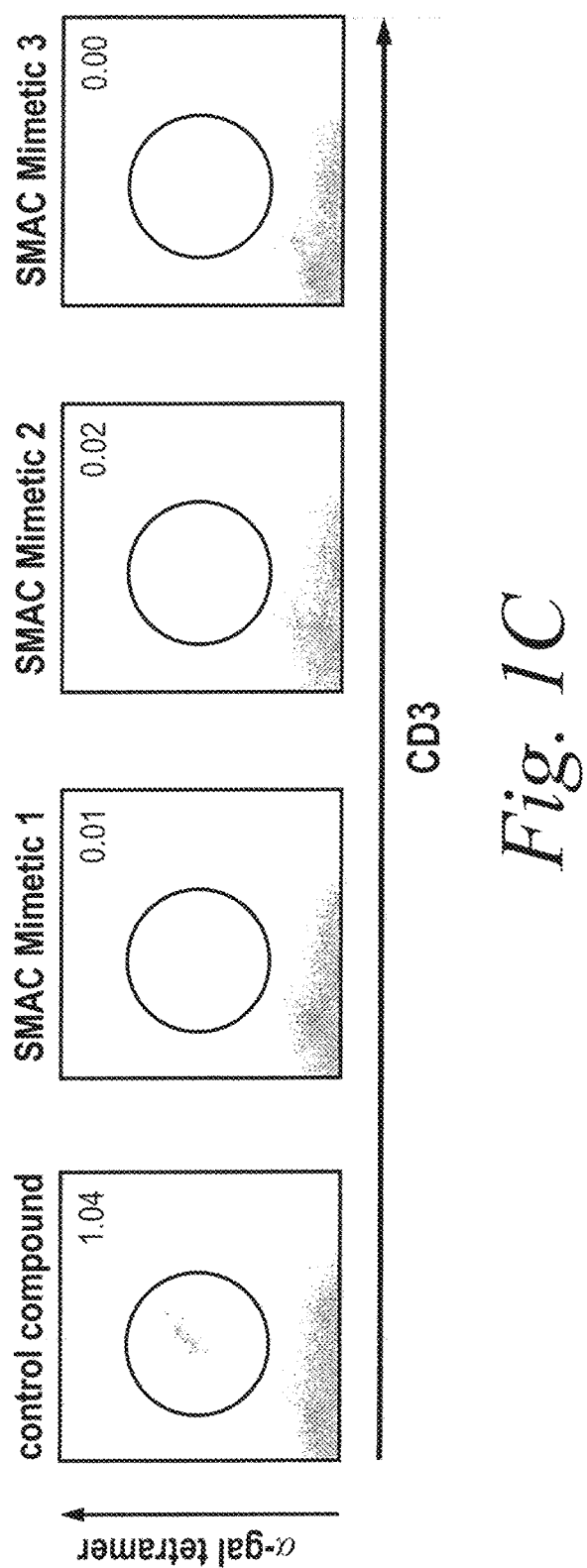
FIG. 1C depicts data, which indicates that NKT cell development in fetal thymic organ culture (FTOC) is blocked by treatment with IAP inhibitors, namely flow cytometry analysis at day 14 FTOCs using α-galcer loaded CD1d tetramers and anti-CD3.
Figure 1D:
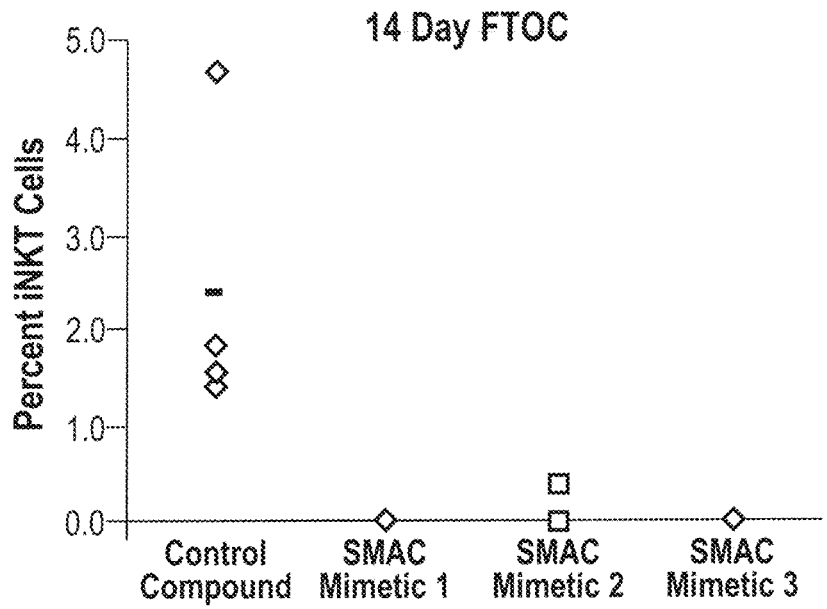
FIG. 1D depicts data, which indicates that NKT cell development in fetal thymic organ culture (FTOC) is blocked by treatment with IAP inhibitors, namely quantification of NKT cell development from several independent experiments.
Figure 1E:
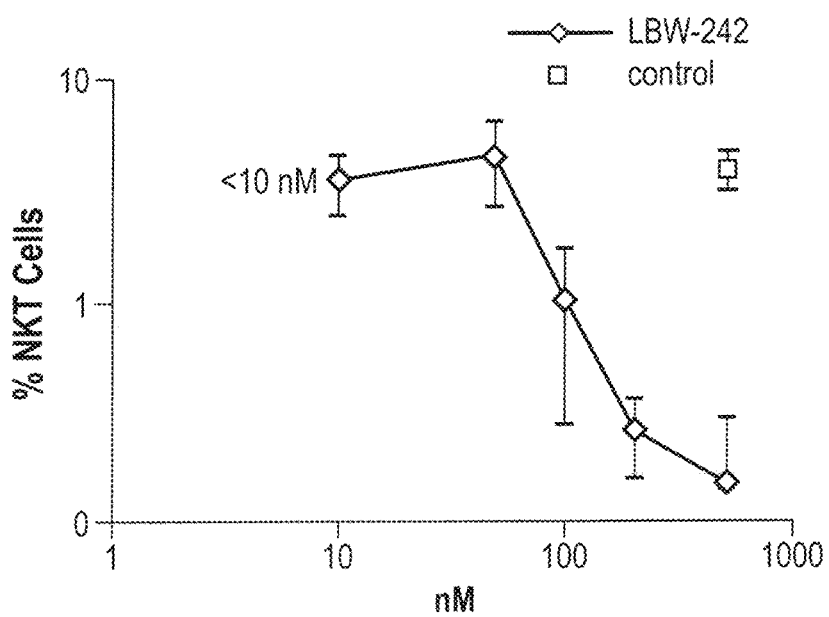
FIG. 1E depicts data, which indicates that NKT cell development in fetal thymic organ culture (FTOC) is blocked by treatment with IAP inhibitors, namely the percent of NKT cells recovered from day 14 FTOCs as a function of LBW-242 dose.

NKT cell development was studied using fetal thymic organ cultures (FTOCs). Embryonic day 16.5 embryos from C57BL/6 mice were cultured in the presence of three distinct IAP inhibitors, a control compound, or vehicle (PBS). After 14 days, cultures were harvested and analyzed by flow cytometry. As shown in FIG. 1, NKT cell development in fetal thymic organ culture (FTOC) is blocked by treatment with IAP inhibitors. FIG. 1A depicts a quantification of thymic populations in FTOCs treated for 14 days with IAP inhibitors (SMAC mimetics). As indicated in FIG. 1A, treatment of FTOCs with IAP inhibitors led to a moderate decrease in CD4+ T cells, with no consistent effect on culture size or on CD8+ and double positive T cells. In multiple experiments, inhibition of IAP family members during FTOC culture completely prevented NKT cell development in a dose-dependent fashion, as shown in FIGS. 1B-D. FIG. 1B depicts single positive thymocyte development at day 14 as a function of LBW-242 concentration. FIG. 1C presents flow cytometry analysis of day 14 FTOCs using α-galcer loaded CD1d tetramers and anti-CD3. The treatment used for each culture is written above the corresponding plot. Data are representative of four independent experiments. FIG. 1D presents a quantification of NKT cell development from several independent experiments using IAP inhibitors. FIG. 1E depicts the percent of NKT cells recovered from day 14 FTOCs as a function of LBW-242 dose. Inhibition of IAP family members did not have a consistent effect on CD1d expression, or on the development of FOXP3 positive T cells or γδ T cells. As used in FIG. 1, SMAC Mimetic 3 is LBW-242; SMAC Mimetics 1 and 2 are additional IAP inhibitor compounds with higher potency than LBW-242. LBW-242 and the control compound were used at 500 nM. SMAC Mimetic 1 and 2 were used at 100 nM. Embryonic day 16.5 C57BL/6 embryos were used for all cultures.

Figure 2C:
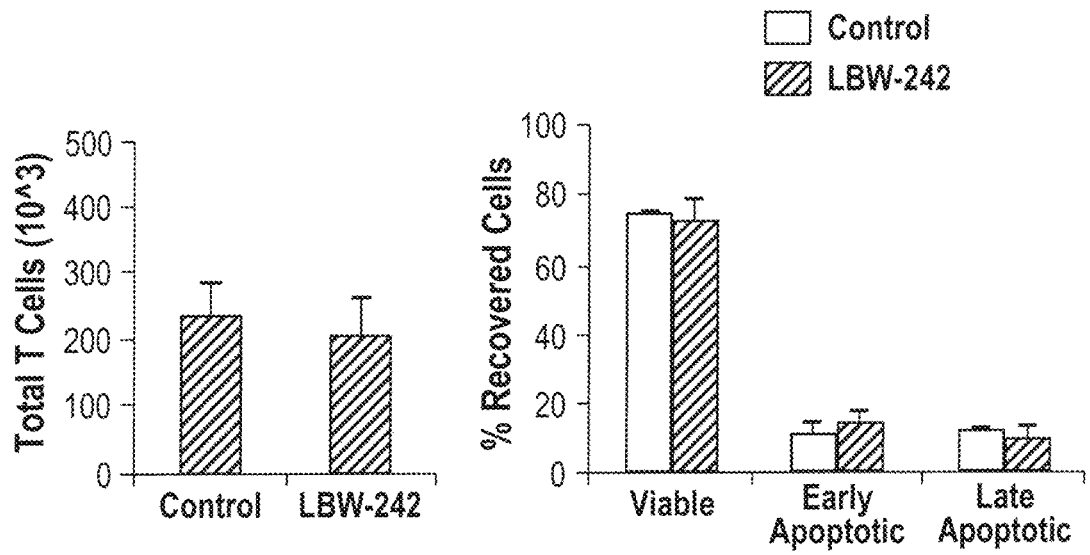
FIG. 2C depicts data, which indicates that inhibition of IAP family members does not sensitize mature CD4+ T cells to apoptosis, namely NKT cells were still detectable in culture at normal frequencies.
Figure 2C:
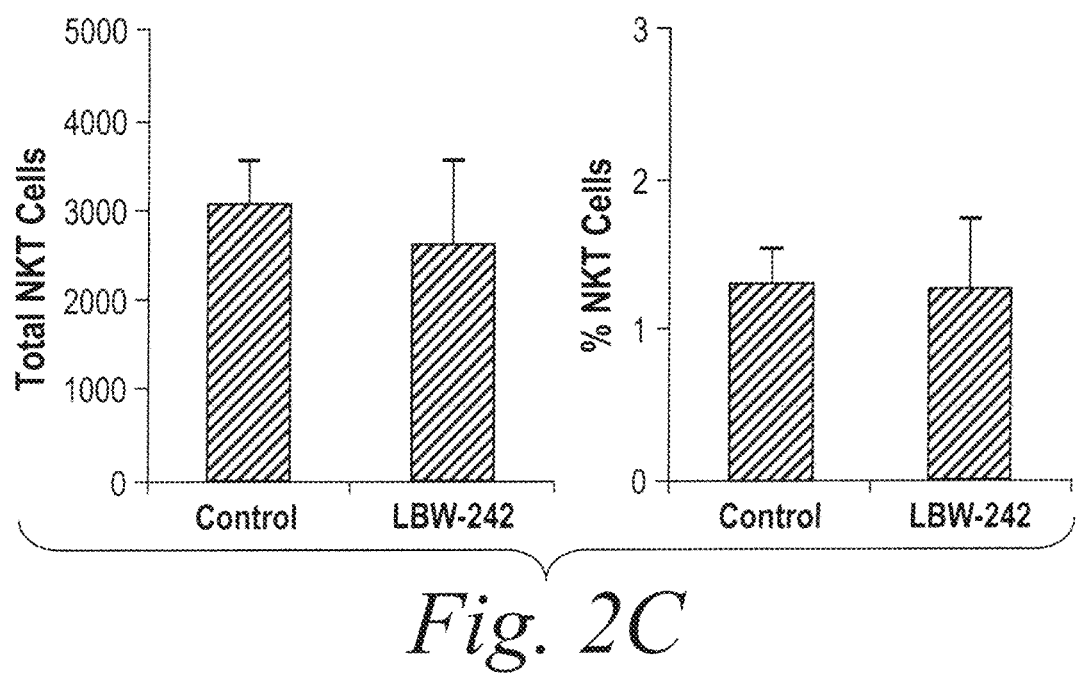

Example 2: Inhibition of IAP Family Members does not Sensitize Mature CD4+ T Cells to Apoptosis The role of IAP family members in mature NKT cell survival was assessed. Spleen-derived CD4+ T cells from BALB/c mice were activated with anti-CD3 and anti-CD28 for 24 hours and then analyzed by flow cytometry. As shown in FIG. 2, inhibition of IAP family members does not sensitize mature CD4+ T cells to apoptosis. $2 \times 10^6$ BALB/c splenic CD4+ T cells were stimulated with anti-CD3 and anti-CD28 in RPMI. After 24 hours viable cells were quantified by trypan blue exclusion, and the resulting cell counts are depicted in FIG. 2A. Apoptotic cells were quantified in the cultures from FIG. 2A using flow cytometry with annexin V and 7-AAD (results are depicted in FIG. 2B). Both LBW-242 and the control compound were used at 500 nM. Treatment of CD4+ T cells with IAP inhibitors did not alter the total number of T cells, nor did it contribute to apoptosis, as shown in FIGS. 2A-B. NKT cells were identified in the cultures from FIG. 2A using anti-CD3 and α-galcer loaded CD1d tetramers. NKT cells were still detectable in culture at normal frequencies, as shown in FIG. 2C. In the absence of stimulation, inhibition of IAP family members also had no discernible effect on apoptosis.

Figure 3A:
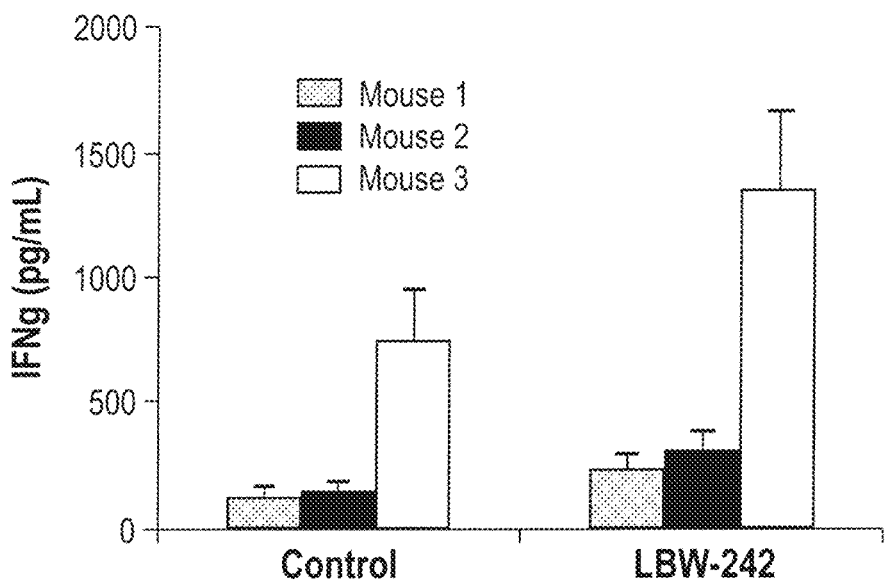
FIG. 3A depicts data, which indicates that inhibition of IAP family members enhances cytokine secretion from activated T cells, namely cytokine levels measured in the culture supernatants.
Figure 3B:
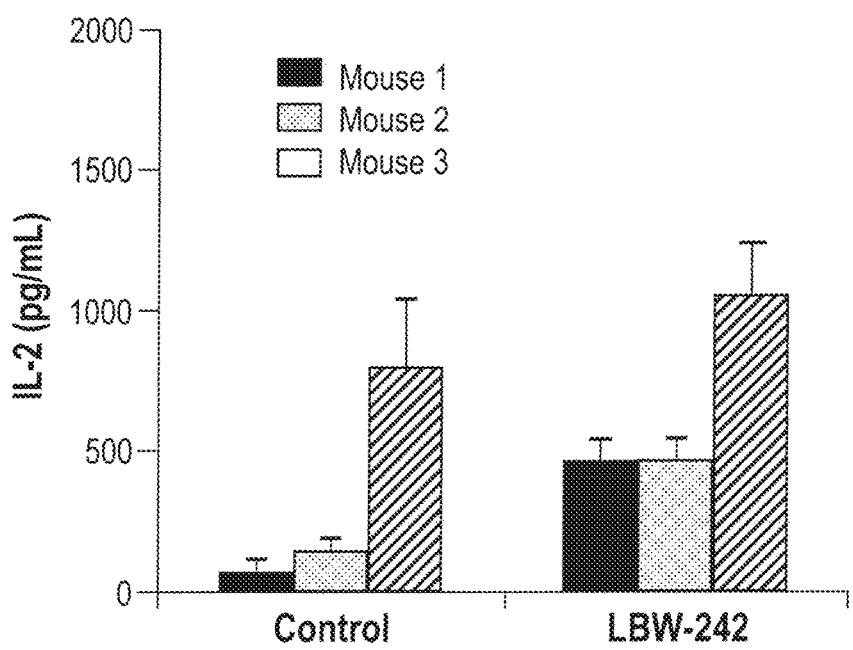
FIG. 3B depicts data, which indicates that inhibition of IAP family members enhances cytokine secretion from activated T cells, namely cytokine levels measured in the culture supernatants.
Figure 3C:
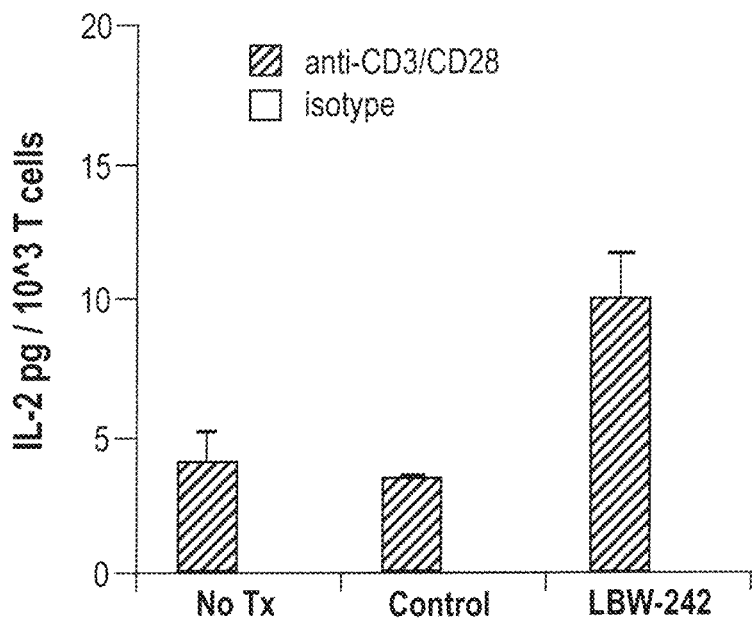
FIG. 3C depicts data, which indicates that inhibition of IAP family members enhances cytokine secretion from activated T cells, namely a similar dose-dependent effect on IL-2 production.
Figure 3D:
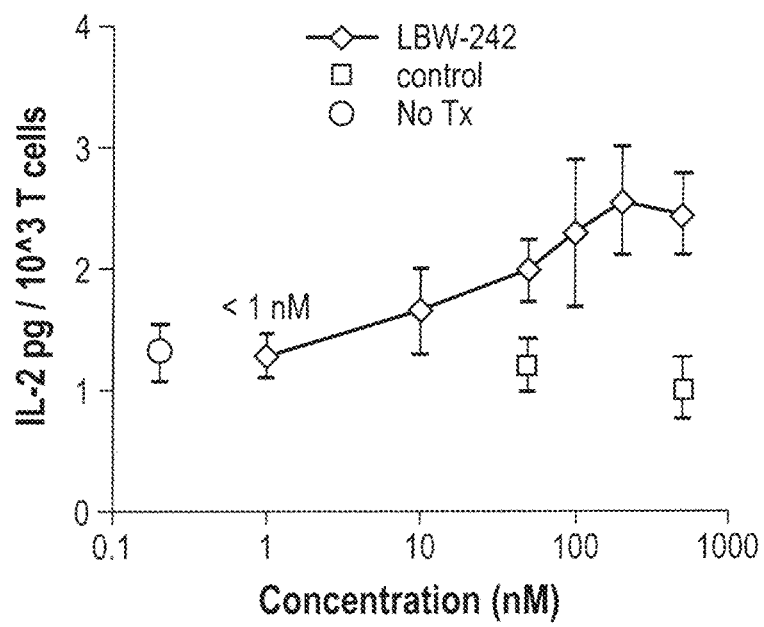
FIG. 3D depicts data, which indicates that inhibition of IAP family members enhances cytokine secretion from activated T cells, namely a similar dose-dependent effect on IL-2 production.

Example 3: Inhibition of IAP Family Members Enhances Cytokine Secretion from Activated T Cells In order to determine the functional consequences of IAP inhibition in NKT cells, spleen cells from BALB/c mice were stimulated with the NKT cell specific agonist α-galactosylceramide (α-galcer). Surprisingly, α-galcer stimulated spleen cells treated with IAP inhibitors showed increased secretion of both IFN-γ (interferon γ) and IL-2 (interleukin-2), as shown in FIGS. 3A-B. $5 \times 10^5$ BALB/c spleen cells from three separate mice were cultured in RPMI with α-galcer in the presence of LBW-242 or a control compound. After 48 hours, cytokine levels were measured in the culture supernatants by ELISA, and the results are depicted in FIG. 3A (IFNγ) and FIG. 3B (IL-2). A similar, dose-dependent effect on IL-2 production was observed in unfractionated BALB/c or C57BL/6 CD4+ T cells stimulated with anti-CD3 and anti-CD28, as shown in FIGS. 3C-D. $10^5$ splenic CD4+ T cells from BALB/c mice were cultured in RPMI with either anti-CD3 and anti-CD28 or isotype control for 48 hours in the presence of LBW-242 or a control compound. IL-2 levels were measured in the culture supernatant by ELISA, as shown in FIG. 3C. A dose response curve for LBW-242 using the conditions described in FIG. 3C is depicted in FIG. 3D. LBW-242 and the control compound were used at 500 nM. No effects from IAP inhibition were observed in the absence of stimulation. Importantly, SMAC mimetic treatment of CD4+ T cells led to enhanced cytokine production even in the presence of the pan-caspase inhibitor ZVAD-FMK, indicating that the observed effect is not the result of release of caspase inhibition.

Figure 4:
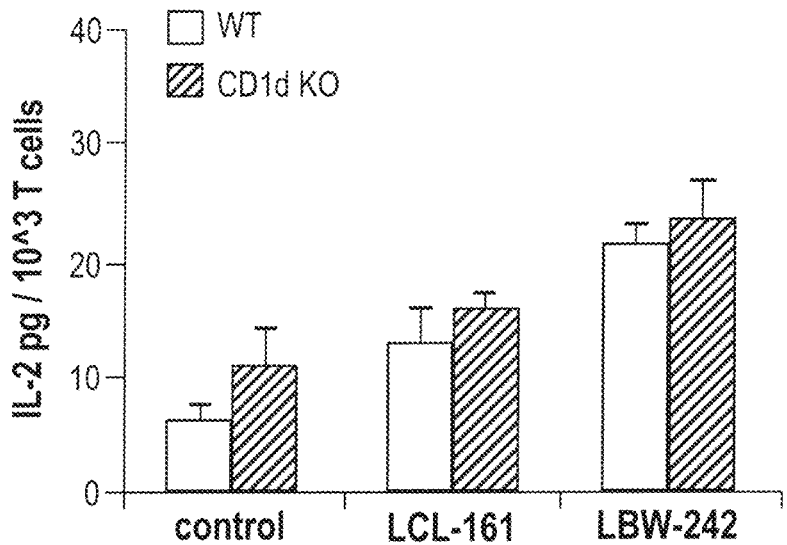
FIG. 4 depicts data which indicates that the enhanced cytokine secretion from activated T cells caused by inhibition of IAP family members is NKT cell independent.
Figure 5:
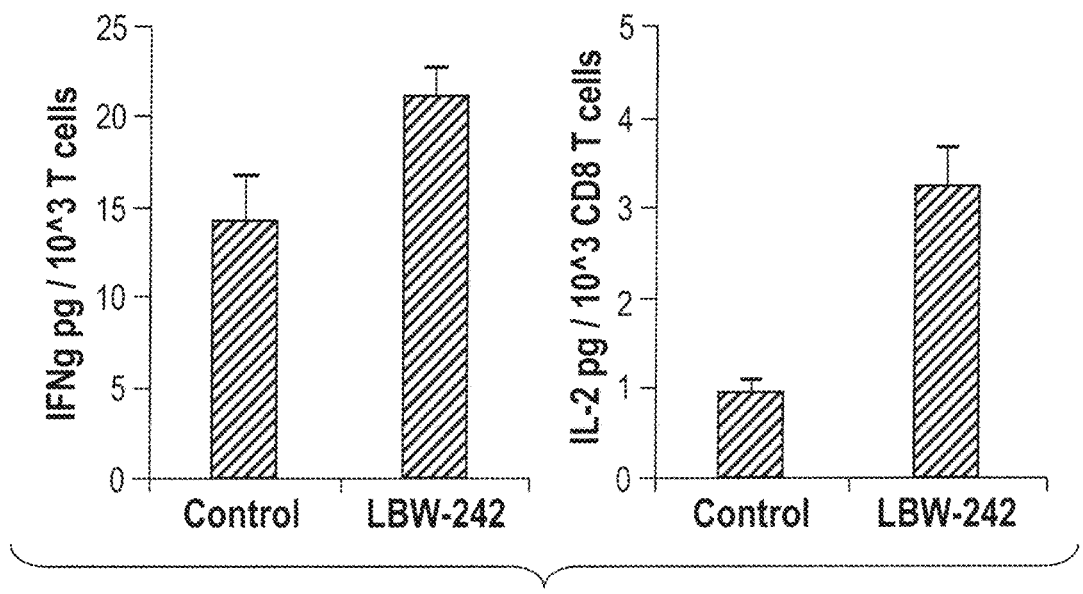
FIG. 5 depicts data which indicates that cytokine production from activated CD8+ T cells is augmented by IAP inhibition.

Because the observed effect of IAP inhibition in T cells could still depend on alterations in NKT cell function, the consequences of IAP inhibition were assessed in NKT cell deficient CD1d knockout C57BL/6 mice. Stimulation of CD1d knockout CD4+ T cells with anti-CD3 and anti-CD28 in the presence of IAP inhibitors led to IL-2 production that was indistinguishable from that of WT animals, indicating that the enhanced cytokine secretion from activated T cells caused by inhibition of IAP family members is NKT cell independent (FIG. 4). CD4+ T cells from spleens of wild-type (WT) and CD1d knockout (KO) C57BL/6 mice were cultured in RPMI with anti-CD3 and anti-CD28 or for 48 hours in the presence of LBW-242, M2, or a control compound. IL-2 levels were measured in the culture supernatant by ELISA, as indicated in FIG. 4. The effect of IAP inhibition was not limited to CD4+ T cells, as CD8+ T cells similarly produced excess IFN-γ and IL-2 after stimulation in the presence of IAP inhibitors (FIG. 5). CD8+ T cells from C57BL/6 mice were cultured in RPMI with anti-CD3 and anti-CD28 or for 48 hours in the presence of LBW-242 or a control compound. Cytokine levels were measured in the culture supernatant by ELISA. As shown in FIG. 5, cytokine production from activated CD8+ T cells is augmented by IAP inhibition.

Example 4: Human CD4+ T Cells Respond to IAP Inhibitors

Figure 6A:
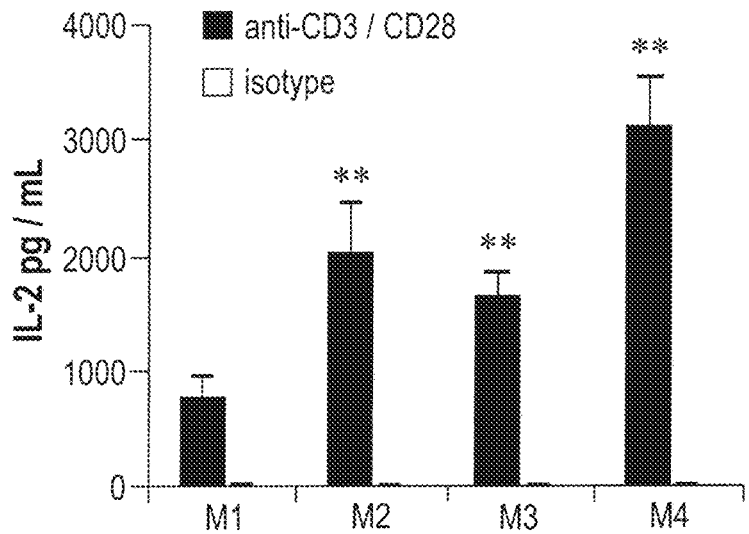
FIG. 6A depicts data, which indicates that human CD4+ T cells respond to IAP inhibitors, namely IL-2 measured by ELISA.
Figure 6B:
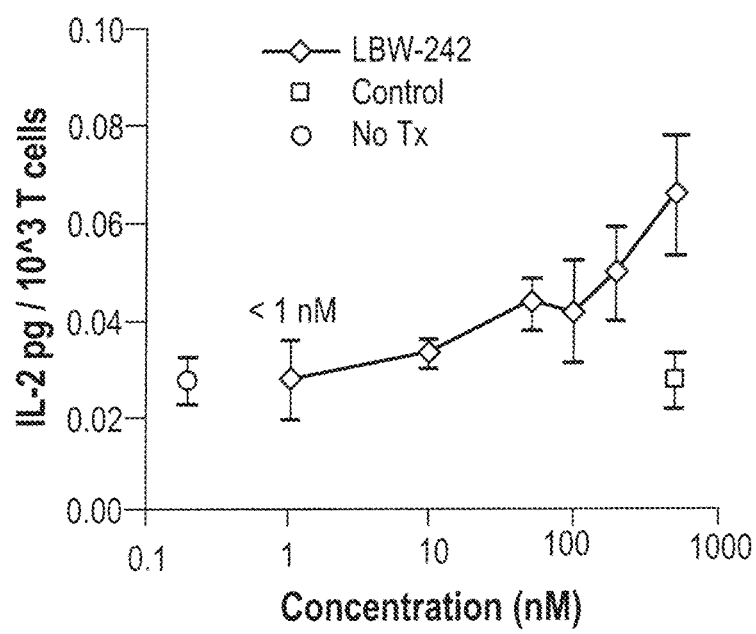
FIG. 6B depicts data, which indicates that human CD4+ T cells respond to IAP inhibitors, namely a dose-response curve for LBW-242.

Most of the members of the IAP family are highly conserved between mouse and human, suggesting that the foregoing observations in the mouse may also apply to activated human cells. In order to address this possibility, CD4+ T cells were purified from the peripheral blood of several healthy volunteers and stimulated with anti-CD3 and anti-CD28 in the presence of IAP inhibitors. As was observed in the mouse, inhibition of IAP family members led to a dose-dependent increase in IL-2 secretion from activated CD4+ T cells; also as was observed in the mouse, IAP inhibition had no apparent effect on resting cells (FIGS. 6A-B). $10^5$ CD4+ T cells were purified from the peripheral blood of a healthy donor and stimulated for 48 hours with either anti-CD3 and anti-CD28, or an isotype control antibody in the presence of IAP inhibitors (M2, M3 and M4) or a control compound (M1). IL-2 was measured by ELISA, as indicated in FIG. 6A. M1 and M4 (LBW-242) were used at 500 nM. M2 and M3 were used at 100 nM. FIG. 6B presents a dose-response curve for LBW-242 using CD4+ T cells from a different donor and the setup described for FIG. 6A.

Figure 6C:
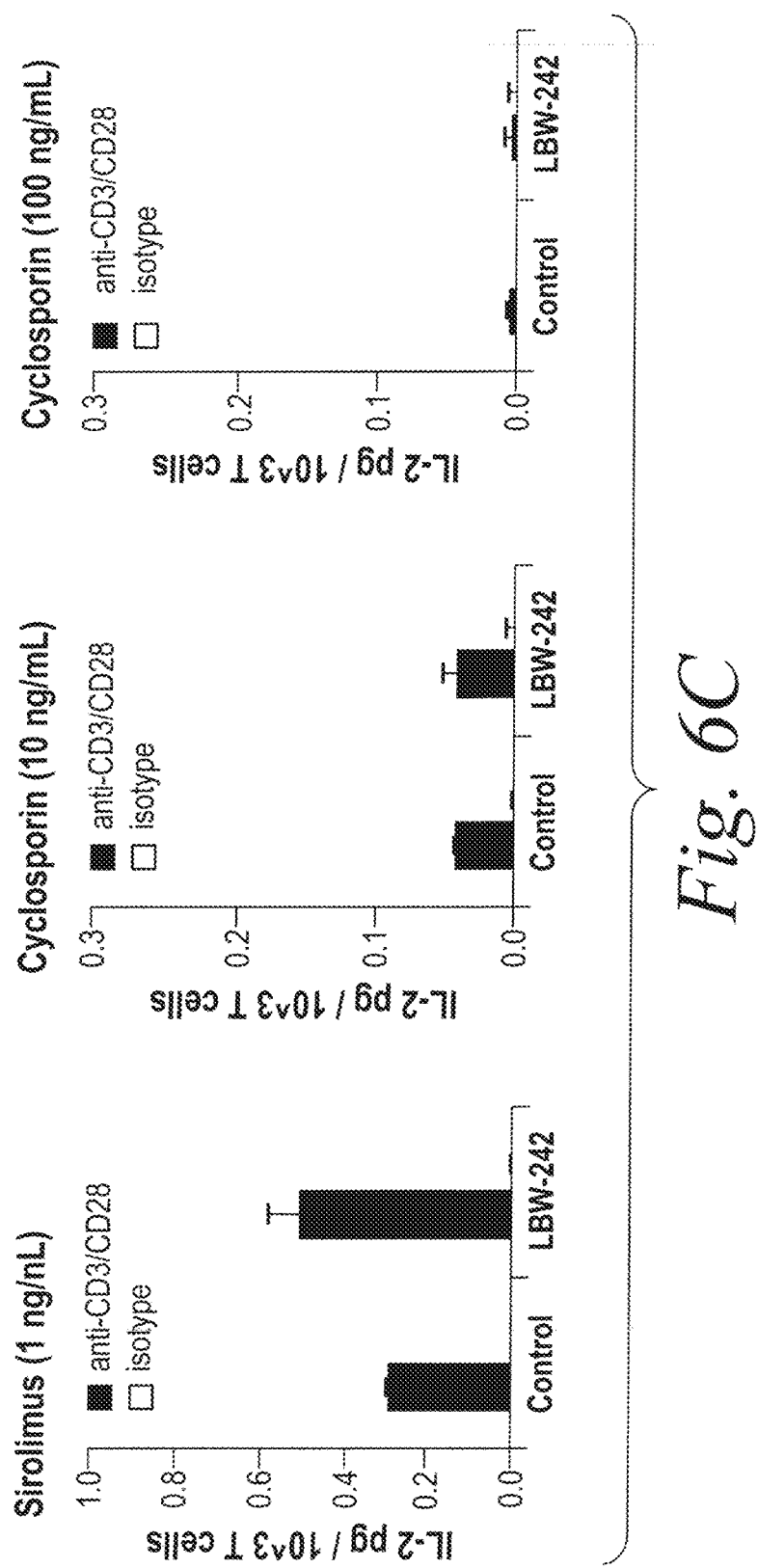
FIG. 6C depicts data, which indicates that human CD4+ T cells respond to IAP inhibitors, namely inhibition of the Akt pathway with rapamycin was able to lower total IL-2 production but did not prevent the enhancement of IL-2 production during IAP inhibition.

Pharmacologic blockade of calcineurin with cyclosporine was able to block the enhanced IL-2 production associated with IAP inhibition. In contrast, inhibition of the Akt pathway with rapamycin was able to lower total IL-2 production, but did not prevent the enhancement of IL-2 production during IAP inhibition (FIG. 6C). Human CD4+ T cells were stimulated in the presence of IAP inhibitors or a control compound with either sirolimus (rapamycin) or cyclosporine, and resulting IL-2 levels are shown in FIG. 6C.

Figure 7:
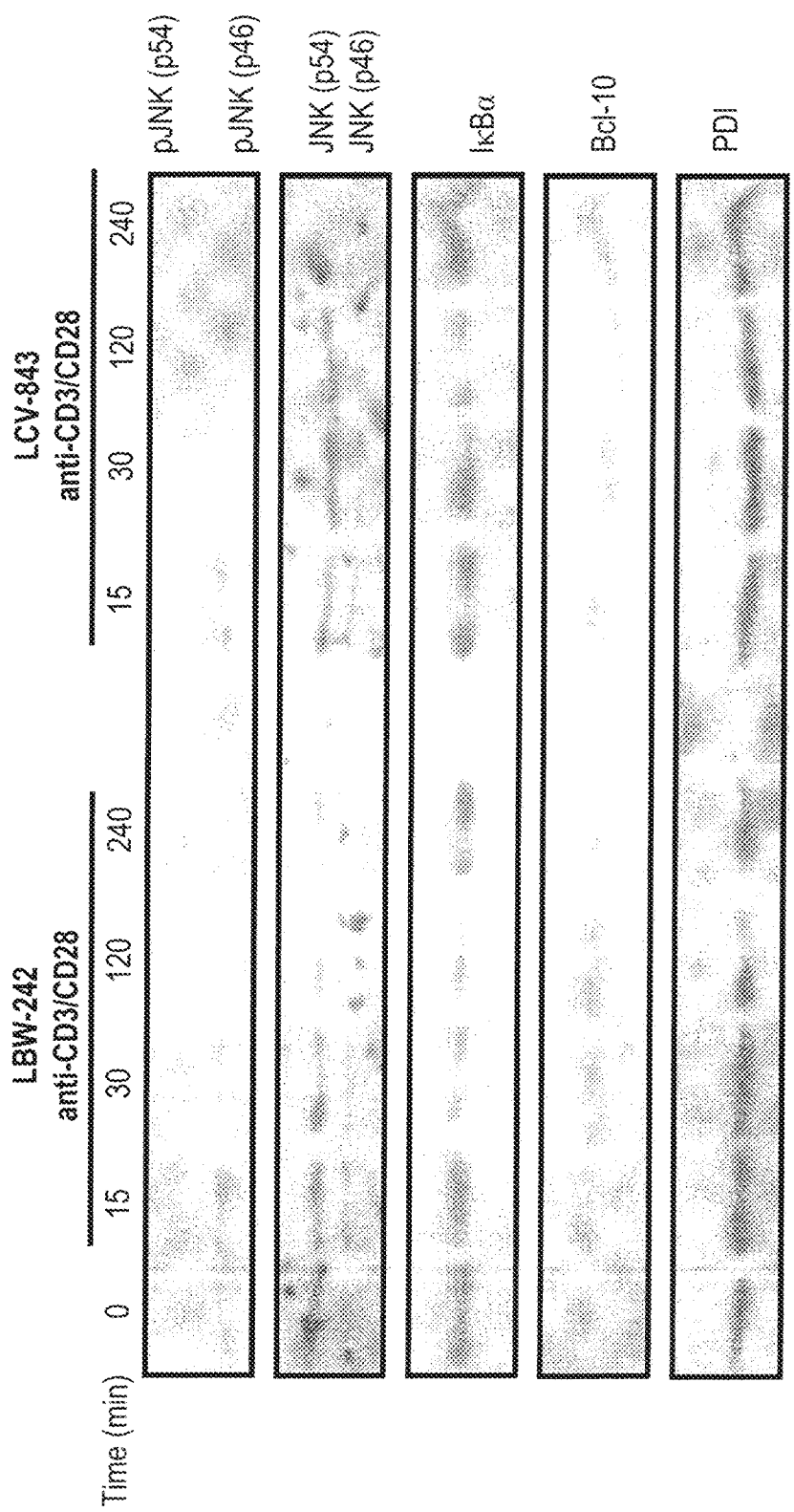
FIG. 7 depicts data which indicates that inhibition of IAP family members during T cell activation leads to enhanced signaling through the JNK and NF-κB pathways.

Example 5: Inhibition of IAP Family Members During T Cell Activation Leads to Enhanced Signaling Through the JNK and NF-κB Pathways In order to investigate the mechanism linking IAP inhibition to enhanced, activation-dependent cytokine production, the effect of IAP inhibition on JNK phosphorylation and IκB degradation in stimulated CD4+ T cells was assessed by Western blot. Both the JNK and NF-κB pathways were activated more rapidly in IAP inhibited T cells, as shown in FIG. 7. Replicate cultures of $2 \times 10^6$ CD4+ T cells were stimulated for the indicated periods of time with anti-CD3 and anti-CD28 in the presence of 500 nM LBW-242 or a control compound (LCV-843). Replicates were combined and cell lysates were analyzed by Western blot for the indicated proteins. PDI was used as a loading control. Although cIAP2 has been reported to be a ubiquitin ligase for bcl-10, IAP inhibition did not lead to a detectable change in bcl-10 levels in activated T cells. No changes in JNK phosphorylation and IκB degradation were observed in T cells treated with IAP inhibitors in the absence of stimulation.

Example 6: IAP Inhibitors Broadly Enhance Immune Cell Activation

Figure 8A:
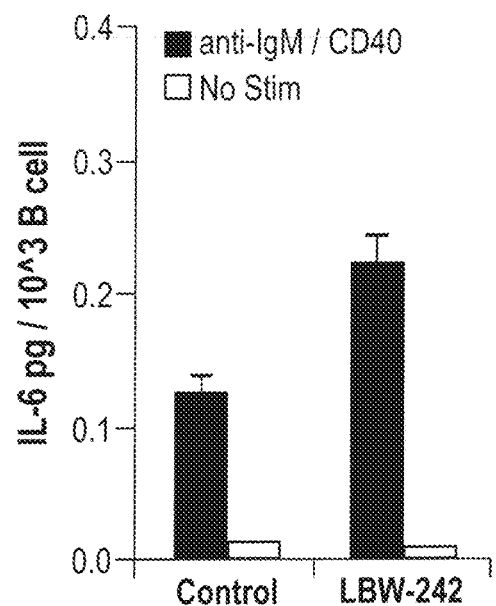
FIG. 8A depicts data, which indicates that IAP inhibitors broadly enhance immune cell activation, namely peritoneal macrophages treated with LPS were found to secrete increased IL-6 when co-treated with IAP inhibitors
Figure 8B:
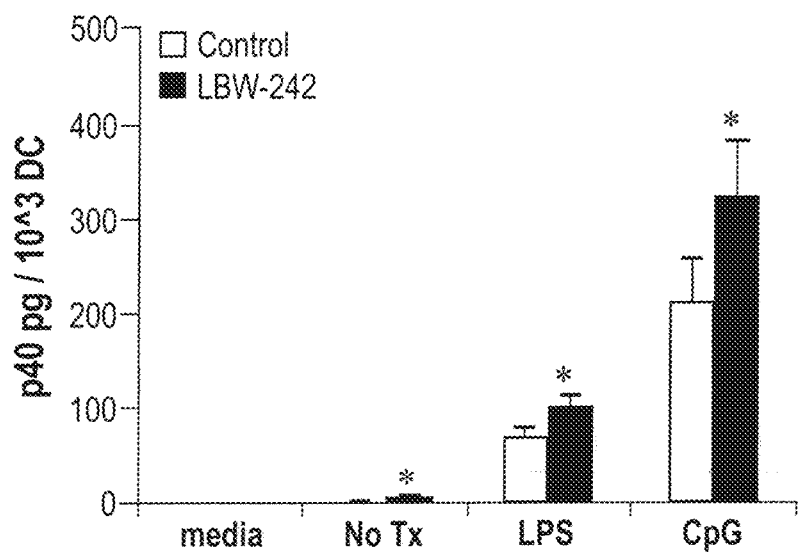
FIG. 8B depicts data, which indicates that IAP inhibitors broadly enhance immune cell activation, namely peritoneal macrophages treated with LPS were found to secrete increased IL-6 when co-treated with IAP inhibitors

Because the JNK and NF-κB pathways play important roles in signaling down stream of a wide range of immune receptors, we analyzed the effect of IAP inhibitors in several additional immune populations. IAP inhibited B cells stimulated with anti-IgM and anti-CD40 produced increased IL-6 compared to control cells, as shown in FIG. 8A. $2 \times 10^6$ B cells were cultured with anti-IgM and anti-CD40 for 96 hours in the presence of LBW-242 or a control compound. IL-6 was measured in the culture supernatant by ELISA. In addition, partially activated (i.e., by cluster disruption) bone marrow derived dendritic cells (DCs) produced increased IL-12 p40 after IAP inhibition; this effect was also observed in IAP inhibited DCs stimulated with LPS or CpG (FIG. 8B). $4 \times 10^4$ partially activated bone marrow derived dendritic cells were cultured with the stimuli indicated in FIG. 8B for 24 hours in the presence of LBW-242 or a control compound. p40 was measured in the culture supernatants by ELISA. For both experiments depicted in FIG. 8, LBW-242 and the control compound were used at 500 nM. Peritoneal macrophages treated with LPS were also found to secrete increased IL-6 when co-treated with IAP inhibitors.

Example 7: Inhibition of IAP Family Members Enhances Allo-Reactivity

Figure 9A:
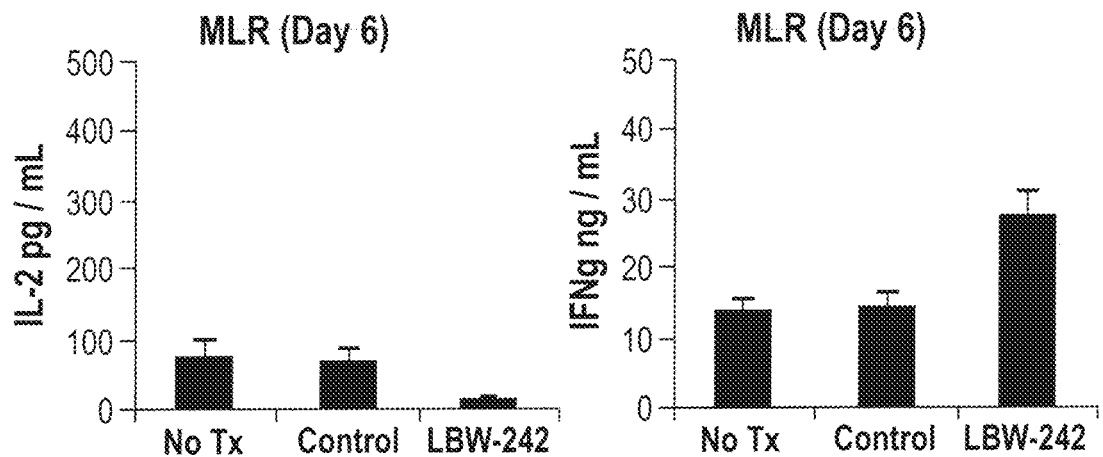
FIG. 9A depicts data, which indicates that inhibition of IAP family members enhances allo-reactivity, namely cultures treated with LBW-242 displayed enhanced IFN-γ secretion; however, IL-2 levels were reduced.
Figure 9B:
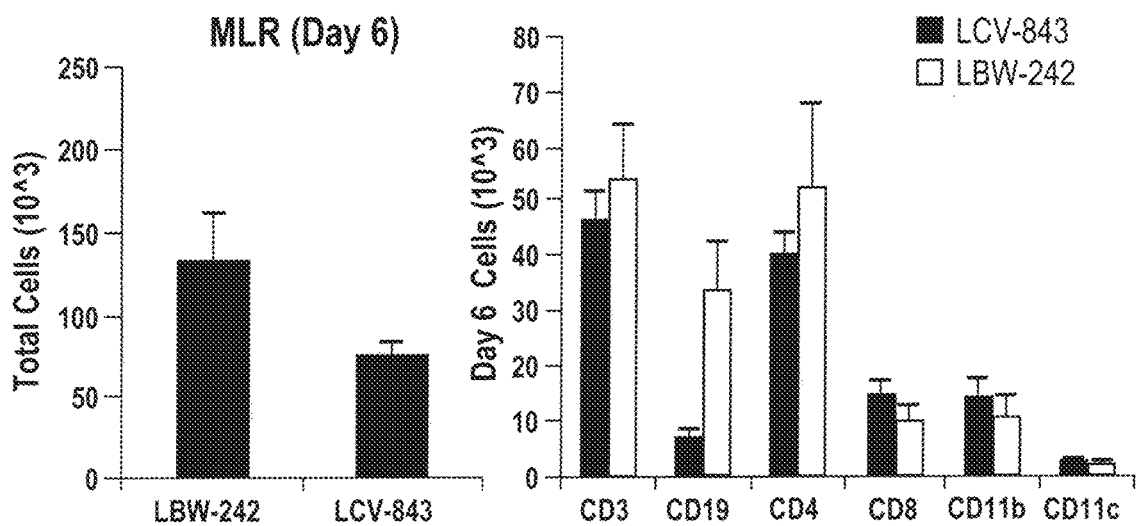
FIG. 9B depicts data, which indicates that inhibition of IAP family members enhances allo-reactivity, namely substantial B cell proliferation occurred in IAP inhibited cultures.

Given the broad ability of IAP inhibition to enhance activation of immune cells, the effect of IAP inhibitors on an allotypic response was examined. $4 \times 10^5$ spleen cells from BALB/c mice were cultured with $8 \times 10^5$ irradiated C57BL/6 spleen cells in the presence of LBW-242 or a control compound (LCV-843). After six days, cultures were harvested and cytokine production and spleen cell proliferation was analyzed. Cultures treated with LBW-242 displayed significantly enhanced IFN-γ secretion; however, IL-2 levels were significantly reduced, as illustrated in FIG. 9A. Cytokines were measured in cell supernatants by ELISA. Both LBW-242 and the control compound were used at 500 nM. At the conclusion of the cultures described in FIG. 9A, total viable cells were counted by trypan blue exclusion and immune cell subsets were identified by flow cytometry using the markers indicated in FIG. 9B. Given that the cultures described in FIG. 9A also exhibited significant CD4 T cell proliferation (FIG. 9B), the decrease in IL-2 is likely due to consumption of the cytokine. Substantial B cell proliferation occurred in IAP inhibited cultures (FIG. 9B).

Figure 10:
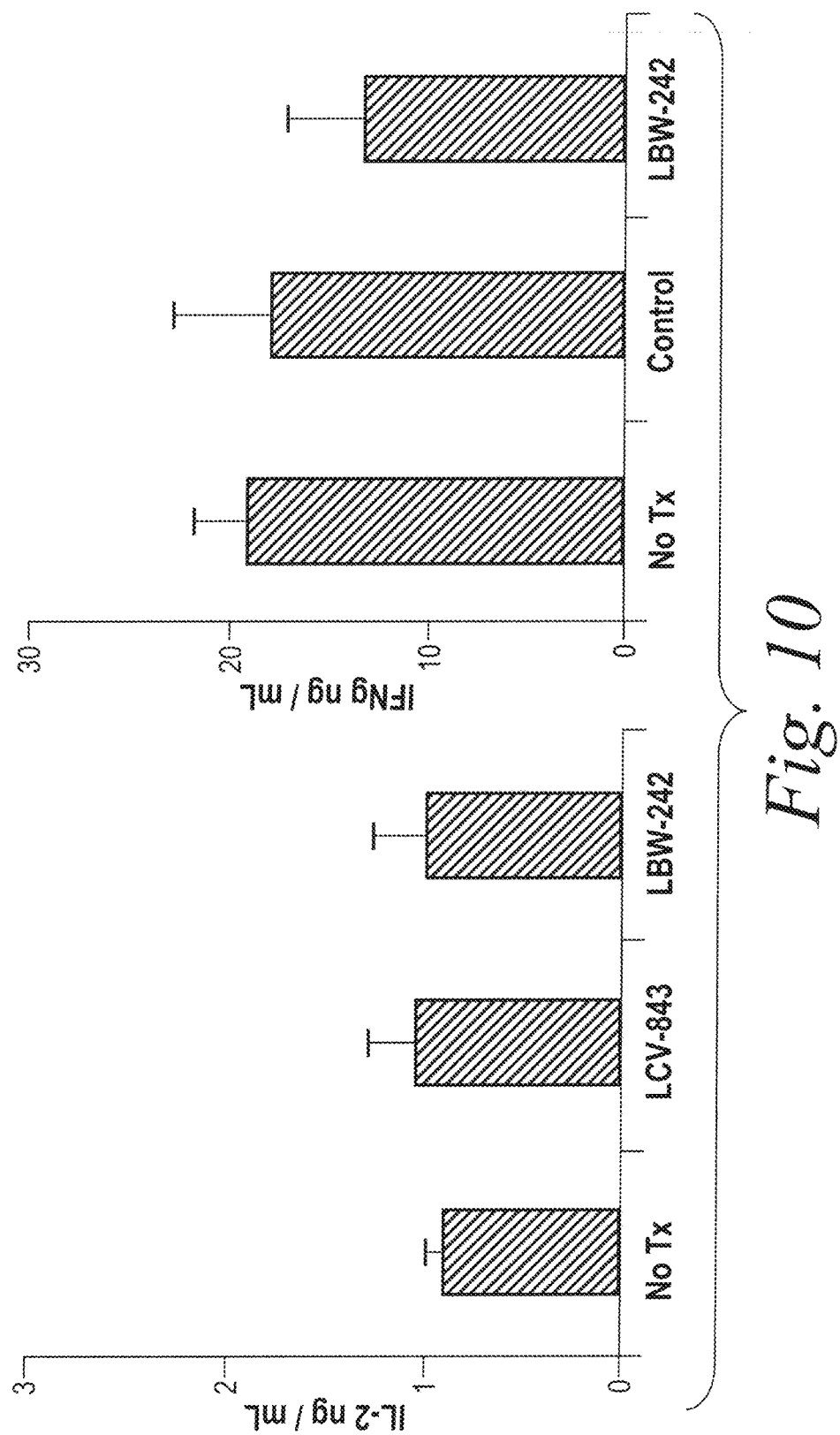
FIG. 10 depicts data which indicates that IAP inhibition is rapidly reversed in restimulated, allo-reactive T cells.

The activation enhancing effects of IAP inhibition were readily reversed; in allo-reactive T cells, secondary stimulations with anti-CD3 in the absence of inhibitors led to equivalent responses regardless of the previous culture conditions (FIG. 10). Cells stimulated in a six day mixed lymphocyte reaction were recovered and restimulated with anti-CD3 for 48 hours. Cytokines were measured in culture supernatants by ELISA. Sample labels indicated in FIG. 10 refer to the treatment used during the primary stimulation.

Figure 11:
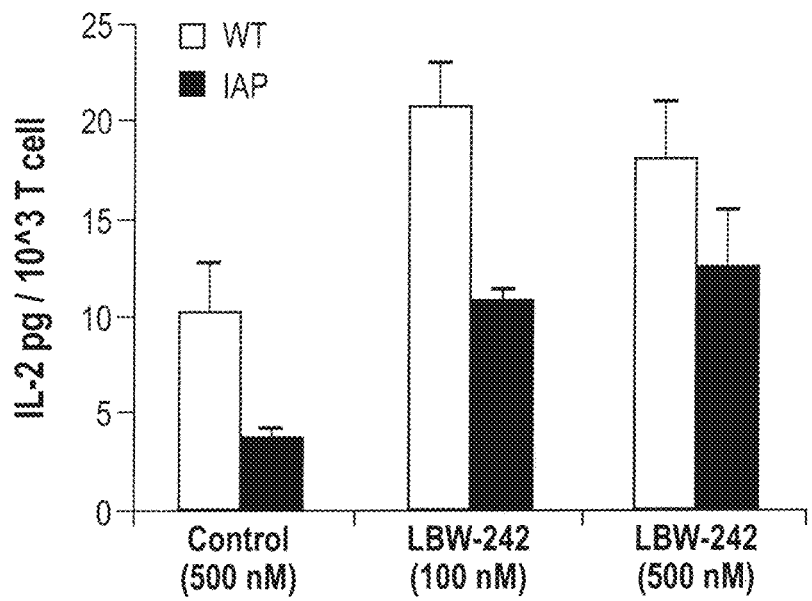
FIG. 11 depicts data which indicates that over-expression of the SMAC binding protein MLIAP in CD4+ T cells leads to decreased production of IL-2 following stimulation.

Example 8: Over-Expression of the SMAC Binding Protein MLIAP in CD4+ T Cells Leads to Decreased Production of IL-2 Following Stimulation Whether overexpression of ML-IAP, an endogenous SMAC binding protein, could alter the response of T cells to activating stimuli was also examined. BALB/c T cells transgenic for ML-IAP secreted reduced levels of IL-2 in response to anti-CD3 and anti-CD28 stimulation, and this effect could be modulated through IAP inhibition, as shown in FIG. 11. $10^5$ CD4+ T cells from BALB/c WT or MLIAP transgenic (IAP) mice were cultured in RPMI with anti-CD3 and anti-CD28 for 48 hours in the presence of LBW-242 or a control compound. IL-2 levels were measured in the culture supernatant by ELISA.

Example 9: XIAP Knockout (KO) T Cells are Resistant to SMAC-Mimetic Treatment

Figure 12:
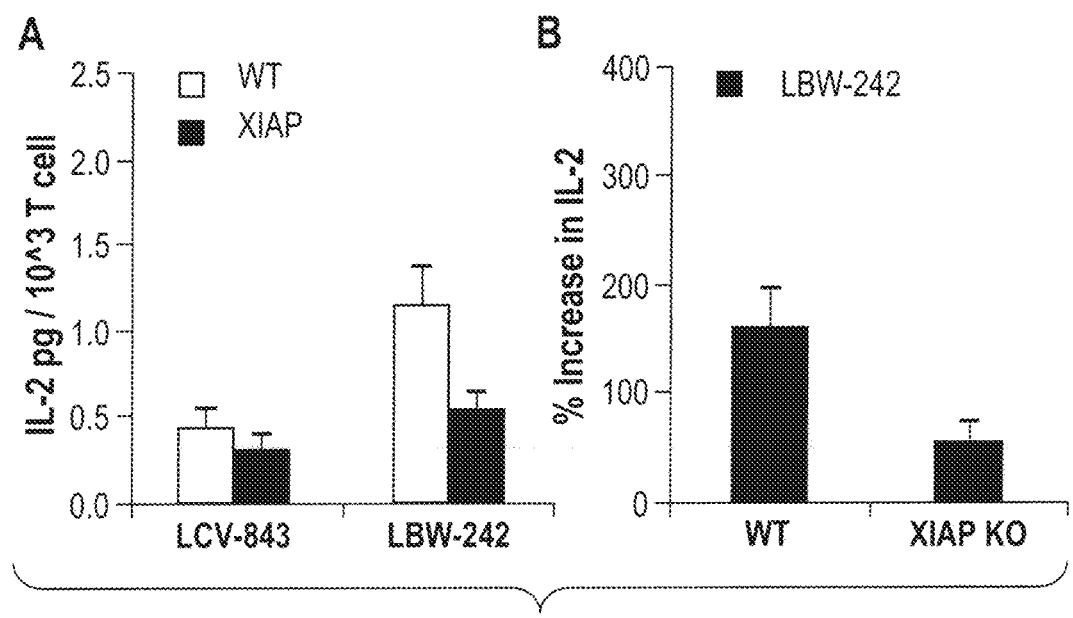
FIG. 12 depicts data which indicates that XIAP knockout (KO) T cells are resistant to SMAC-mimetic treatment.

In order to establish specificity for the IAP-dependent effect on T cell activation, T cells from XIAP deficient mice were activated in the presence of LBW-242 or the control compound LCV-843. At baseline, XIAP deficient T cells secreted IL-2 and levels comparable to WT animals; however, XIAP deficient cells were resistant to SMAC-mimetic treatment, displaying only a small increase in cytokine secretion upon treatment with LBW-242 (FIG. 12). As shown in FIG. 12A, $10^5$ CD4+ T cells from C57BL/6 WT or XIAP KO mice were cultured in RPMI with anti-CD3 and anti-CD28 for 48 hours in the presence of LBW-242 or the control compound LCV-843. IL-2 levels were measured in the culture supernatant by ELISA. FIG. 12B depicts the ratio of IL-2 produced from CD4+ T cells stimulated in the presence of LBW-242 compared to LCV-843. These results indicate that XIAP plays an important role in sensitizing T cells to SMAC mimetic treatment.

Figure 13:
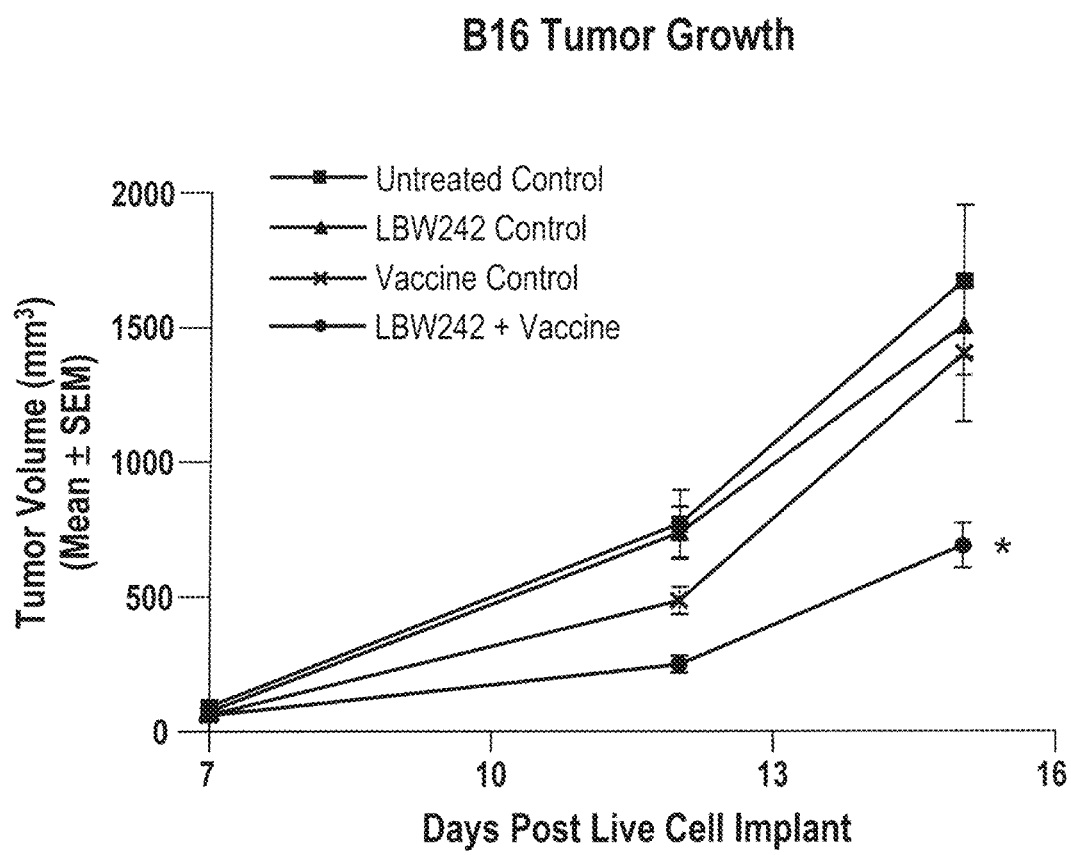
FIG. 13 depicts data which indicates that IAP inhibitors enhance immune activation in vivo, and improve protective immunity following vaccination.

Example 10: IAP Inhibitors Enhance Immune Activation and Improve Protective Immunity Following Vaccination In Vivo To examine the effect of IAP inhibitors on immune activation in vivo, LBW-242 was administered to mice in combination with a vaccine prior to subsequent challenge. Irradiated B16 mouse melanoma cells (vaccine) were administered to mice on days −14 and −7 with or without a single oral dose of LBW-242 (150 mg/kg). Live B16 tumor cells were implanted into the mice on day 0 (challenge). Tumor volume was measured at 7, 10, 13 and 16 days following the live cell implant. As shown in FIG. 13, mice that received the IAP inhibitor LBW-242 in combination with the B16 vaccine had a reduced tumor burden following challenge with live B16 cells, compared with mice that received either LBW-242 or the B16 vaccine alone. This data indicates that administration of an IAP inhibitor in combination with an antigen improves immune activation, enhancing protective immunity.

Example 11: Synthesis of the IAP Inhibitors of the Invention

Described below is a synthesis procedure for LBW 242 (N-[1-cyclohexyl-2-oxo-2-(6-phenethyl-octahydro-pyrrolo [2,3-c]pyridin-1-yl)-ethyl]-2-methylamino-propionamide).

Analogous synthesis procedures can be used to prepare the other IAP inhibitors of the invention.

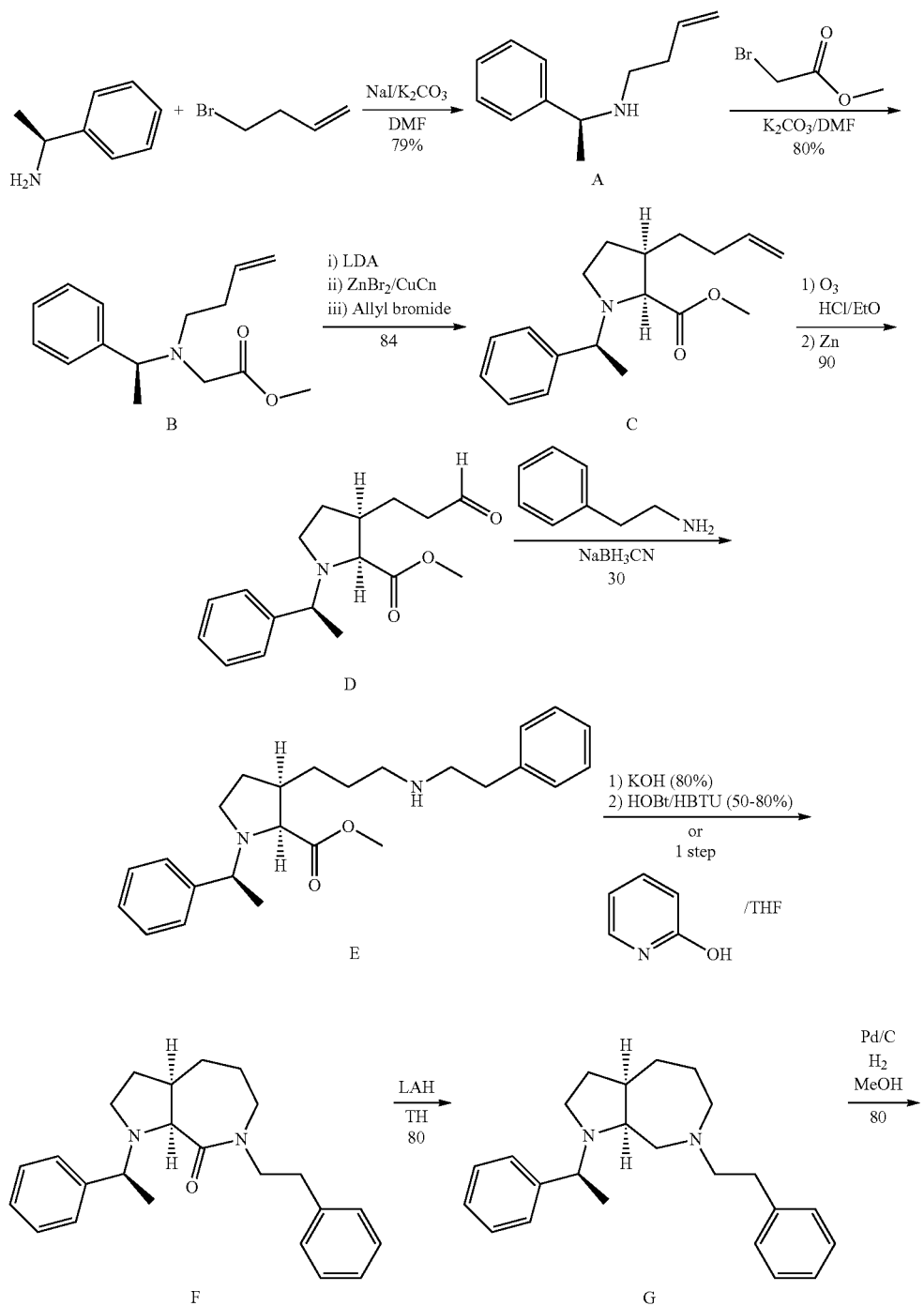

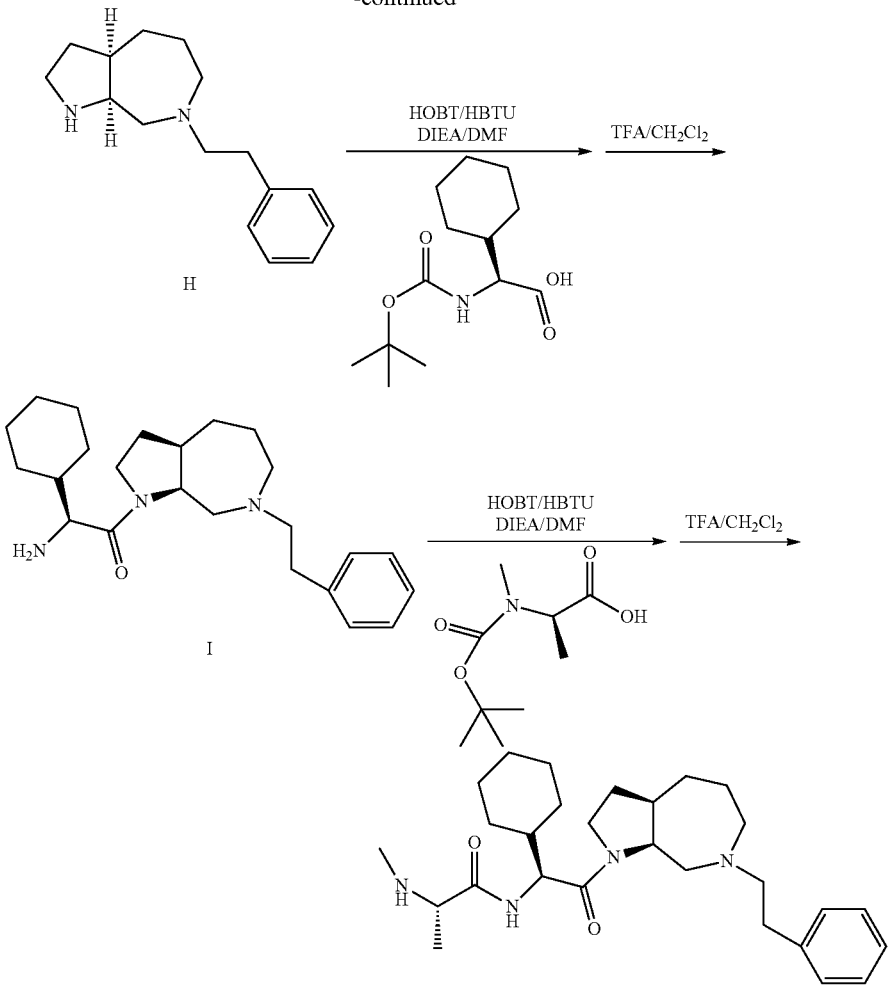

But-3-enyl-((S)-1-phenyl-ethyl)-amine (A)

To a solution of S-(−)-1-phenyl ethylamine (15.75 g, 130 mmol) in 150 mL of DMF at 0° C. is added $K_2CO_3$ (53.9 g, 390 mmol) in small portions. After stirring at 0° C. for 10 min, 4-bromobutene (13.5 g, 100 mmol) is added dropwise and followed by NaI (58.5 g, 390 mmol) in small portions. The reaction mixture, a white suspension, is heated to 95° C. and stirred overnight/16 hrs. The solution is cooled to RT and diluted with 200 mL of ether, and washed with 3×100 ml of water. The organic layer is dried over $Na_2SO_4$ and concentrated. The crude product is purified by distillation (65~70° C. under high vacuum) to yield a colorless liquid (13.5 g, 76.7%).

[But-3-enyl-((S)-1-phenyl-ethyl)-amino]-acetic acid ethyl ester (B)

To a solution of But-3-enyl-((S)-1-phenyl-ethyl)-amine (6.37 g, 36.4 mmol) in 150 mL of DMF at 0° C. is added $K_2CO_3$ (10.0 g, 72.8 mmol) in small portions. After stirring at 0° C. for 10 min, ethylbromoacetate (8.35 g, 54.6 mmol) is added slowly. The reaction mixture, a white suspension, is stirred at r.t. overnight/16 hrs. The solution is diluted with 200 mL of ether, and washed with 3×100 ml of water. The crude product is purified by chromatography (hexane/$CH_2Cl_2$:50/50) to give a pale liquid (8.5 g, 94.5%).

(2S,3R)-3-But-3-enyl-1-((S)-1-phenyl-ethyl)-pyrrolidine-2-carboxylic acid ethyl ester (C)

To a solution of diisopropylamine (3.6 g, 35.7 mmol) in THF (80 mL) at −40° C. is added BuLi (14.28 mL, 35.7 mmol, 2.5 M in hexane) slowly. The solution is warmed to 0° C. and stirred for 30 min to form an LDA solution. The LDA solution is cooled to −70° C. and added to a solution of [But-3-enyl-((S)-1-phenyl-ethyl)-amino]-acetic acid ethyl ester (7.8 g, 29.8 mmol) in THF (80 mL) slowly at −70° C. The light yellowish reaction solution is stirred at −20° C. for 30 min to become a deep yellow solution, and then cooled to −70° C. To the solution is added $ZnBr_2$ (16.76 g, 74.5 mmol) in ether (50 mL) dropwise at −70° C. After stirring at RT for 1.5 hrs, the reaction solution is cooled to 0° C. and added a solution of CuCN (3.47 g, 38.74 mmol) and LiCl (3.29 g, 77.48 mmol) in THF (80 ml) slowly. After stirring at 0° C. for 10 min, allyl bromide (7.26 g, 60 mmol) is added dropwise to the reaction solution, and warmed very slowly to r.t. After stirring overnight at r.t., the reaction is quenched by addition of 60 mL of saturated $NH_4Cl$ and extracted with 3×150 mL of ether. The combined organic layers are concentrated. The crude product is purified by chromatography (hexane/EtOAc: 85/15) to give a colorless liquid (7.4 g, 82.6%). ($ZnBr_2$ is dried at 150° C. under high vacuum for 1 hour before use.)

(2S,3R)-1-((2E,4Z)—(S)-1)₂-Dimethyl-hexa-2,4-dienyl)-3-(3-oxo-propyl) pyrrolidine-2-carboxylic acid ethyl ester (D)

(2S,3R)-3-But-3-enyl-1-((S)-1-phenyl-ethyl)-pyrrolidine-2-carboxylic acid ethyl ester(1.0 g, 3.32 mmol) is dissolved in EtOH (10 mL) with HCl (0.5 mL, 37%), and cooled to −70° C. Ozone gas is bubbled though the solution for about 10 min or until the solution is turned very light blue color. The nitrogen gas is bubbled though the solution for 15 min to remove excess ozone in the solution. To the cool solution is added Zn dust (0.43 g. 6.6 mmol) and HCl (0.5 mL, 37%), and stirred at r.t. for 20 min. After filtration the solution is diluted with 50 mL of $CH_2Cl_2$ and washed with saturated $NaHCO_3$ (10 mL) and 2×20 ml of water. After dried and concentrated, a colorless liquid (1.0 g) is obtained without further purification for next step reaction.

(2S,3R)-3-(3-Phenethylamino-propyl)-1-((S)-1-phenyl-ethyl)-pyrrolidine-2-carboxylic acid ethyl ester (E)

To a solution of (2S,3R)-1-((2E,4Z)—(S)-1,2-Dimethyl-hexa-2,4-dienyl)-3-(3-oxo-propyl) pyrrolidine-2-carboxylic acid ethyl ester (1.g, crude) in EtOH(IO mL) is added phenethylamine(0.44 g, 3.65 mmol) at r.t. After stirring at r.t. for 30 min, $NaBH_3CN$ (0.3 g, 4.87 mmol) is added in one portion. After stirring at r.t. for 1.5 Hrs, the reaction solution is diluted with 50 mL of ether and washed with 20 mL of brine. The ether layer is concentrated and the crude product is purified by chromatography ($CH_2Cl_2$/MeOH: 97/3) to give a pale liquid (405 mg, 30.0%).

(3aS57aS)-6-Phenethyl-1-((S)-1-phenyl-ethyl)-octahydro-pyrrolo[2,3-c]pyridin-7-one (F)

(2S,3R)-3-(3-Phenethylamino-propyl)-1-((S)-1-phenyl-ethyl)-pyrrolidine-2-carboxylic acid ethyl ester(340 mg, 0.83 mmol) is dissolved in 20 mL of $MeOH/KOH/H_2O$ (10 mL/5 g/5 mL). After stirring at 80° C. for 2 hrs, the solution is cooled to 0° C. and neutralized by addition of HCl (37%) to pH=5. After concentration the crude product is dissolved in 1 mL of $CH_2Cl_2$, and filtered through a short silica gel plug and eluted with $CH_2Cl_2$/MeOH (93/7) to give a pale glassy solid (250 mg, 78.9%) as the acid.

To a solution (0.05-0.1 M) of acid (1 equivalent) in DMF at r.t. is added diisopropylethylamine (5 equivalents). After stirring at r.t. for 20 min, a solution (0.05~0.1 M) of HOBT (1.2 equivalents) and HBTU (1.2 equivalents) in DMF is added to the reaction mixture, and continued to be stirred for 1.5 h (or monitored by TLC). The reaction solution is diluted with ether (1×5~10 times by volume of the solution), and washed with water (twice ×3 by volume of the solution). The combined organic solution is concentrated. The crude product is diluted with $CH_2Cl_2$ and dried over Na2SO4, and purified by chromatography($CH_2Cl_2$/MeOH:97/3) to give pure product (70-95% yield).

Procedure for Compound F Using 2-Hydroxyl Pyridine:

A solution of (2S,3R)-3-(2-Phenethylamino-ethyl)-1-((S)-1-phenyl-ethyl)-pyrrolidine-2 carboxylic acid methyl ester(400 mg, 1.05 mmol) and 2-hydroxyl pyridine(100 mg, 1.05 mmol) in THF(I O mL) is stirred at 40° C. for 24 hrs. The reaction is diluted with 50 mL of ether and washed with 2×120 mL of water. After dried and concentrated to give a pale liquid (350 mg) without further purification for next step reaction.

(3aR,8aS)-7-Phenethyl-1-((S)-1-phenyl-ethyl)-decahydro-pyrrolo[2,3-c]azepine (G)

To a solution(0.02M) of lactam (1 equivalent) in THF at −20° C. is added a solution (0.02M) of $LiAlH_4$ (2 equivalent) in THF slowly. After stirring at r.t. for 1.5 hrs, the solution is diluted with ether (1×5 times by volume of the solution) and washed with water (twice 2 times by volume of the solution), dried and concentrated. The crude product is purified by chromatography ($CH_2Cl_2$/MeOH:97/3) to give product (yield 70-90%).

(3aR,8aS)-7-Phenethyl-decahydro-pyrrolo[2,3-c]azepine (H)

A solution/suspension of reactant (<1 g) and Pd 10% on carbon (20% by weight) in MeOH (10 mL, with 2 drops of acetic acid) in a 1000 ml round flask is vigorously stirred at r.t. under hydrogen gas (at atmosphere pressure) from a balloon for 4-8 hrs. After degassed by house vacuum for 10 min, the reaction mixture is filtered to remove catalyst and concentrated. The crude product is diluted with $CH_2Cl_2/H_2O$ (8/2, reasonable amount) and neutralized with 10% $NH_4OH$ to pH=7-8. After dried and concentrated to give product (80%-quantitative yield) without purification for the next step reaction.

LBW 242:

Prepared from compound H using the scheme described below:

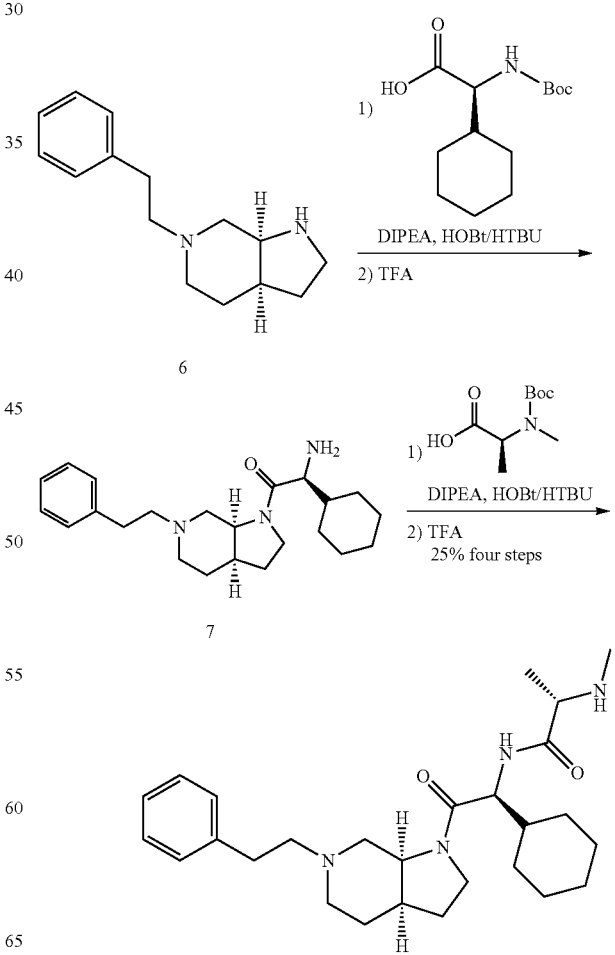

Compound (7):

To a solution of 6 in dichloromethane (25 mL) is added sequentially diisopropylethylamine (4.17 mL, 24 mmol), t-Boc-L-cyclohexylglycine (1.54 g, 6 mmol), and a solution of 0.45 M HOBt/HBTU in DMF (16 mL, 7.19 mmol). The mixture is stirred overnight at room temperature, then diluted with EtOAc (200 mL) and washed sequentially with 1 M aq. citric acid (50 mL), water (50 mL), aq. Sat. NaHCO$_3$ (50 mL) and brine (2×50 mL). The organic layer is dried and concentrated under vacuum. The residue is purified by flash chromatography (silica gel; Hexane/EtOAc 1:9) to provide a yellow oil. The yellow oil is dissolved in dichloromethane (20 mL), TFA (10 mL) is added and the mixture is stirred at room temperature for 3 h. The mixture is concentrated and the residue is dissolved in dichloromethane (100 mL) and neutralized with saturated sodium bicarbonate. The solution is extracted with dichloromethane (3×50 mL). The organic extracts are combined, dried and concentrated under vacuum to provide 1.75 g (79% two steps) of the title compound which is used in next step without further purification or characterization.

LBW 242:

To a solution of 7 (1.75 g, 4.74 mmol) in dichloromethane (25 mL) is added sequentially diisopropylethylamine (3.30 mL, 19 mmol), t-Boc-N-methyl-L-alanine (0.97 g, 4.74 mmol), and a solution of 0.45 M HOBt/HBTU in DMF (13 mL, 5.691 mmol). The mixture is stirred overnight at room temperature. The mixture is diluted with EtOAc (200 mL) and washed sequentially with 1 M citric acid (50 mL), water (50 mL), aq. Sat. NaHCO$_3$ (50 mL) and brine (2×50 mL). The organic layer is dried and concentrated under vacuum. The residue is dissolved in dichloromethane (20 mL), TFA (10 ml) is added and the mixture is stirred at room temperature for 3 hours. The mixture is concentrated and the residue is dissolved in dichloromethane (100 mL) and neutralized with saturated sodium bicarbonate. The solution is extracted with dichloromethane (3×50 mL). The organic extracts are combined, dried and concentrated under vacuum. The residue is purified by HPLC (C-18 silica gel, 20% CH$_3$CN/H$_2$O in 0.5% TFA) to provide g (36% two steps) of the title compound as TFA salt.

EQUIVALENTS

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

INCORPORATION BY REFERENCE

The entire contents of all patents, published patent applications, websites, and other references cited herein are hereby expressly incorporated herein in their entireties by reference.

What is claimed:
1. An immune enhancing complex comprising:
(a) a compound of Formula I:

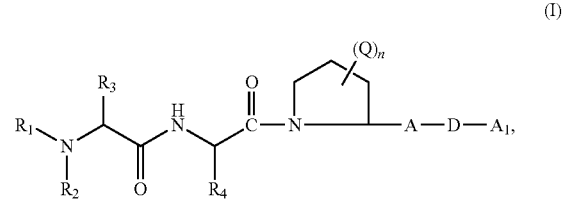

(I)

or pharmaceutically acceptable salts, enantiomers, stereoisomers, rotamers, tautomers, diastereomers, or racemates thereof;
wherein
$R_1$ is H, $C_1$-$C_4$ alkyl, $C_2$-$C_4$ alkenyl, $C_2$-$C_4$ alkynyl or $C_3$-$C_{10}$ cycloalkyl, wherein $R_1$ may be unsubstituted or substituted;
$R_2$ is H, $C_1$-$C_4$ alkyl, $C_2$-$C_4$ alkenyl, $C_2$-$C_4$ alkynyl, $C_3$-$C_{10}$ cycloalkyl, wherein $R_2$ may be unsubstituted or substituted;
$R_3$ is H, $CF_3$, $C_2F_5$, $C_1$-$C_4$ alkyl, $C_2$-$C_4$ alkenyl, $C_2$-$C_4$ alkynyl, $CH_2$—Z, or
$R_2$ and $R_3$, taken together with the nitrogen atom to which they are attached, form a heterocyclic ring,
wherein the alkyl, alkenyl, alkynyl groups or het ring may be unsubstituted or substituted;
Z is H, OH, F, Cl, $CH_3$, $CH_2Cl$, $CH_2F$ or $CH_2OH$;
$R_4$ is $C_{1-10}$ alkyl, $C_{1-10}$ alkenyl, $C_{1-10}$ alkynyl, $C_3$-$C_{10}$ cycloalkyl, wherein the $C_{1-10}$ alkyl, or cycloalkyl groups are unsubstituted or substituted;
A is het, which may be substituted or unsubstituted;
D is $C_1$-$C_7$ alkylene or $C_2$-$C_9$ alkenylene, C(O), O, NR$_7$, S(O)$_r$, C(O)—$C_1$-$C_{10}$ alkyl, O—$C_1$-$C_{10}$ alkyl, S(O)$_r$—$C_1$-$C_{10}$ alkyl, C(O)C$_0$-$C_{10}$ arylalkyl, OC$_0$-$C_{10}$ arylalkyl, or S(O)$_r$C$_0$-$C_{10}$ arylalkyl,
wherein alkyl and aryl groups may be unsubstituted or substituted;
r is 0, 1 or 2;
$A_1$ is a substituted or unsubstituted aryl or unsubstituted or substituted het, wherein substituents on aryl and het are halo, alkyl, lower alkoxy, NR$_5$R$_6$, CN, NO$_2$ or SR$_5$;
each Q is independently H, $C_1$-$C_{10}$ alkyl, $C_1$-$C_{10}$ alkoxy, aryl $C_1$-$C_{10}$ alkoxy, OH, O—$C_1$-$C_{10}$ alkyl, (CH$_2$)$_{0-6}$—$C_3$-$C_7$ cycloalkyl, aryl, aryl $C_1$-$C_{10}$ alkyl, O—(CH$_2$)$_{0-6}$ aryl, (CH$_2$)$_{0-6}$ het, het, O—(CH$_2$)$_{0-6}$ het, C(O)R$_{11}$, —C(O)N(R$_{11}$)(R$_{12}$), N(R$_{11}$)(R$_{12}$), SR$_{11}$, S(O)R$_{11}$, S(O)$_2$ R$_{11}$, S(O)$_2$—N(R$_{11}$)(R$_{12}$), or NR$_{11}$—S(O)$_2$—(R$_{12}$), wherein alkyl, cycloalkyl and aryl are unsubstituted or substituted;
n is 0, 1, 2 or 3, 4, 5, 6 or 7;
$R_{11}$ and $R_{12}$ are independently H, $C_1$-$C_{10}$ alkyl, (CH$_2$)$_{0-6}$—$C_3$-$C_7$ cycloalkyl, (CH$_2$)$_{0-6}$—(CH)$_{0-1}$(aryl)$_{1-2}$, C(O)—$C_1$-$C_{10}$ alkyl, —C(O)—(CH$_2$)$_{1-6}$—$C_3$-$C_7$ cycloalkyl, —C(O)—O—(CH$_2$)$_{0-6}$-aryl, —C(O)—(CH$_2$)$_{0-6}$—O-fluorenyl, C(O)—NH—(CH$_2$)$_{0-6}$-aryl, C(O)—(CH$_2$)$_{0-6}$-aryl, C(O)—(CH$_2$)$_{1-6}$-het, —C(S)—$C_1$-$C_{10}$alkyl, —C(S)—(CH$_2$)$_{1-6}$—$C_3$-$C_7$ cycloalkyl, —C(S)—O—(CH$_2$)$_{0-6}$-aryl, —C(S)—(CH$_2$)$_{0-6}$—O-fluorenyl, C(S)—NH—(CH$_2$)$_{0-6}$-aryl, —C(S)—(CH$_2$)$_{0-6}$-aryl or C(S)—(CH$_2$)$_{1-6}$-het, C(O)R$_{15}$, C(O)NR$_{15}$R$_{16}$, C(O)OR$_{15}$, S(O)$_m$R$_{15}$, S(O)$_m$NR$_{15}$R$_{16}$, m=1 or 2, C(S)R$_{15}$, C(S)NR$_{15}$R$_{16}$, C(S)OR$_{15}$, wherein alkyl, cycloalkyl and aryl are unsubstituted or substituted; or $R_{11}$ and $R_{12}$ are a substituent that facilitates transport of the molecule across a cell membrane, or $R_{11}$ and $R_{12}$ together with the nitrogen atom form het, wherein the alkyl substituents of $R_{11}$ and $R_{12}$ may be unsubstituted or substituted by one or more substituents selected from $C_1$-$C_{10}$ alkyl, halogen, OH, O—$C_1$-$C_6$ alkyl, —S—$C_1$-$C_6$ alkyl, $CF_3$ or $NR_{15}R_{16}$;

substituted cycloalkyl substituents of $R_{11}$ and $R_{12}$ are substituted by one or more substituents selected from a $C_2$-$C_{10}$ alkene; $C_1$-$C_6$ alkyl; halogen; OH; O—$C_1$-$C_6$ alkyl; S—$C_1$-$C_6$ alkyl, $CF_3$; or $NR_{15}R_{16}$ and substituted het or substituted aryl of $R_{11}$ and $R_{12}$ are substituted by one or more substituents selected from halogen, hydroxy, $C_1$-$C_4$ alkyl, $C_1$-$C_4$ alkoxy, nitro, CNO—C(O)—$C_1$-$C_4$alkyl and C(O)—O—$C_1$-$C_4$-alkyl;

$R_5$, $R_6$ and $R_7$ are independently hydrogen, lower alkyl, aryl, aryl lower alkyl, cycloalkyl, or cycloalkyl lower alkyl, $C(O)R_{15}$, $S(O)R_{15}$, $C(O)OR_{15}$, $C(O)NR_{15}R_{16}$; and the substituents on $R_1$, $R_2$, $R_3$, $R_4$, Q, and A and Ai groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, arylsulfonyl, aryl-lower alkylsulfonyl, lower aryl alkyl lower alkylarylsulfonyl, halogen-lower alkylmercapto, halogen-lower alkylsulfonyl, phosphono (—P(=O)(OH)$_2$), hydroxy-lower alkoxy phosphoryl or di-lower alkoxyphosphoryl, $(R_9)NC(O)$—$NR_{10}R_{13}$, lower alkyl carbamic acid ester or carbamates or —$NR_8R_{14}$, wherein $R_8$ and $R_{14}$ can be the same or different and are independently H or lower alkyl, or $R_8$ and $R_{14}$, together with the N atom, form a 3- to 8-membered heterocyclic ring containing nitrogen heteroring atoms and may optionally contain one or two additional heteroring atoms selected from nitrogen, oxygen and sulfur, wherein the heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbarmoyl, N-lower or N,N-dilower alkyl carbamoyl, mercapto, or lower alkylthio;

$R_9$, $R_{10}$ and $R_{13}$ are independently hydrogen, lower alkyl, halogen substituted lower alkyl, aryl, aryl lower alkyl, halogen substituted aryl, halogen substituted aryl lower alkyl;

wherein $R_{15}$ and $R_{16}$ are independently hydrogen, lower alkyl, aryl, aryl lower alkyl, cycloalkyl, or cycloalkyl lower alkyl; and het is a 5- to 7-membered monocyclic heterocyclic ring containing 1-4 heteroring atoms selected from N, O and S or an 8- to 12-membered fused ring system that includes one 5- to 7-membered monocyclic heterocyclic ring containing 1, 2 or 3 heteroring atoms selected from N, O and S, wherein het is unsubstituted or substituted; and (b) an immune cell, wherein the compound of Formula I is capable of enhancing an immune activity of the immune cell.

2. An immune enhancing complex comprising:
(a) a compound of Formula II:

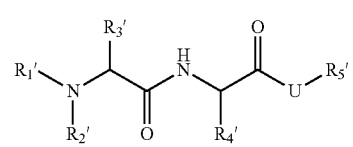

(II)

or pharmaceutically acceptable salts, enantiomers, stereoisomers, rotamers, tautomers, diastereomers, or racemates thereof;

wherein $R_1'$ is H;

$R_2'$ is $C_1$-$C_4$ alkyl; which may be unsubstituted or substituted;

$R_3'$ is $C_1$-$C_4$ alkyl;

$R_4'$ is —$C_3$-$C_{10}$cycloalkyl; which may be unsubstituted or substituted;

$R_5'$ is H; $C_1$-$C_{10}$-alkyl; aryl; phenyl; $C_3$-$C_7$cycloalkyl; —$(CH_2)_{1-6}$—$C_3$-$C_7$cycloalkyl; —$C_1$-$C_{10}$alkyl-aryl; —$(CH_2)_{0-6}$—$C_3$-$C_7$cycloalkyl-$(CH_2)_{0-6}$-phenyl; —$(CH_2)_{0-4}$CH—$((CH_2)_{1-4}$-phenyl)$_2$; —$(CH_2)_{0-6}$—CH(phenyl)$_2$, -indanyl; —C(O)—$C_1$-$C_{10}$alkyl; —C(O)—$(CH_2)_{1-6}$—$C_3$-$C_7$-cycloalkyl; —C(O)—$(CH_2)_{0-6}$-phenyl; —$(CH_2)_{0-6}$—C(O)-phenyl; —$(CH_2)_{0-6}$-het; —C(O)—$(CH_2)_{1-6}$-het; or $R_5'$ is a residue of an amino acid, wherein the alkyl, cycloalkyl, phenyl and aryl substituents are unsubstituted or substituted;

U is as shown in structure III:

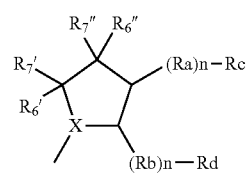

(III)

wherein $R_5'$ is attached to Rc or Rd;

each n is, independently, 0-5;

X is C or N;

Ra and Rb are independently an O, S, or N atom or $C_{0-8}$ alkyl wherein one or more of the carbon atoms in the alkyl chain may be replaced by a heteroatom selected from O, S or N, and where the alkyl may be unsubstituted or substituted;

Rd is selected from:

(a) -Re-Q-(Rf)$_p$(Rg)$_q$; or (b) $Ar_1$-D-$Ar_2$;

Rc is H or Rc and Rd may together form a cycloalkyl or het; where if Rd and Rc form a cycloalkyl or het, $R_5'$ is attached to the formed ring at a C or N atom;

p and q are independently 0 or 1;

Re is C$_{1-8}$ alkyl or alkylidene, and Re which may be unsubstituted or substituted;

Q is N, O, S, S(O), or S(O)$_2$;

Ar$_1$ and Ar$_2$ are substituted or unsubstituted aryl or het;

Rf and Rg are each independently H; —C$_1$-C$_{10}$alkyl; C$_1$-C$_{10}$alkylaryl; —OH; —O—C$_1$-C$_{10}$alkyl; —(CH$_2$)$_{0-6}$—C$_3$-C$_7$cycloalkyl; —O—(CH$_2$)$_{0-6}$-aryl; phenyl; aryl; phenyl-phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S(O)—R$_{11}$; —S(O)$_2$—R$_{11}$; —S(O)$_2$—NR$_{11}$R$_{12}$; —NR$_{11}$—S(O)$_2$—R$_{12}$; S—C$_1$-C$_{10}$alkyl; aryl-C$_1$-C$_4$alkyl; het-C$_1$-C$_4$-alkyl wherein alkyl, cycloalkyl, het and aryl are unsubstituted or substituted; —SO$_2$—C$_1$-C$_2$alkyl; —SO$_2$—C$_1$-C$_2$alkylphenyl; —O—C$_1$-C$_4$alkyl; or R$_g$ and Rf form a ring selected from het or aryl;

D is —CO—; —C(O)—C$_{1-7}$ alkylene or arylene; —CF$_2$—; —O—; —S(O)$_r$ where r is 0-2; 1,3-dioxaxolane; or C$_{1-7}$ alkyl-OH; where alkyl, alkylene or arylene may be unsubstituted or substituted with one or more halogens, OH, —O—C$_1$-C$_6$alkyl, —S—C$_1$-C$_6$alkyl or —CF$_3$; or D is —N(Rx)- wherein Rx is H; C$_{1-7}$ alkyl (unsubstituted or substituted); aryl; —O(C$_{1-7}$cycloalkyl) (unsubstituted or substituted); C(O)—C$_1$-C$_{10}$alkyl; C(O)—C$_0$-C$_{10}$alkyl-aryl; C—O—C$_1$-C$_{10}$alkyl; C—O—C$_0$-C$_{10}$alkyl-aryl or SO$_2$—C$_1$-C$_{10}$-alkyl; SO$_2$—(C$_0$-C$_{10}$-alkylaryl);

R$_6$", R$_7$", R$_6$' and R$_7$' are each independently H; —C$_1$-C$_{10}$ alkyl; —C$_1$-C$_{10}$ alkoxy; aryl-C$_1$-C$_{10}$ alkoxy; —OH; —O—C$_1$-C$_{10}$alkyl; —(CH$_2$)$_{0-6}$—C$_3$-C$_7$cycloalkyl; —O—(CH$_2$)$_{0-6}$-aryl; phenyl; —(CH$_2$)$_{1-6}$-het; —O—(CH$_2$)$_{1-6}$-het; —OR$_{11}$'; —C(O)—N(R$_{11}$')(R$_{12}$'); —N(R$_{11}$')(R$_{12}$'); —S(O)$_2$—R$_{11}$'; —NR$_{11}$'—S(O)$_2$—R$_{12}$; wherein alkyl, cycloalkyl and aryl are unsubstituted or substituted; and R$_6$", R$_7$", R$_6$' and R$_7$' can be united to form a ring system;

R$_{11}$' and R$_{12}$' are independently H; C$_1$-C$_{10}$ alkyl; —(CH$_2$)$_{0-6}$—C$_3$-C$_7$cycloalkyl; —(CH$_2$)$_{0-6}$—(CH)$_{0-1}$(aryl)$_{1-2}$; —C(O)—C$_1$-C$_{10}$alkyl; —C(O)—(CH$_2$)$_{1-6}$—C$_3$-C$_7$cycloalkyl; —C(O)—O—(CH$_2$)$_{0-6}$-aryl; —C(O)—(CH$_2$)$_{0-6}$—O-fluorenyl; —C(O)—NH—(CH$_2$)$_{0-6}$-aryl; —C(O)—(CH$_2$)$_{0-6}$-aryl; —C(O)—(CH$_2$)$_{1-6}$-het; —C(S)—C$_1$-C$_{10}$alkyl; —C(S)—(CH$_2$)$_{1-6}$—C$_3$-C$_7$cycloalkyl; —C(S)—O—(CH$_2$)$_{0-6}$-aryl; —C(S)—(CH$_2$)$_{0-6}$—O-fluorenyl; —C(S)—NH—(CH$_2$)$_{0-6}$-aryl; —C(S)—(CH$_2$)$_{0-6}$-aryl; —C(S)—(CH$_2$)$_{1-6}$-het; wherein alkyl, cycloalkyl and aryl are unsubstituted or substituted; or R$_{11}$' and R$_{12}$' are a substituent that facilitates transport of the molecule across a cell membrane; or R$_{11}$' and R$_{12}$' together with the nitrogen atom form het;

wherein the alkyl substituents of R$_{11}$' and R$_{12}$' may be unsubstituted or substituted by one or more substituents selected from C$_1$-C$_{10}$alkyl, halogen, OH, —O—C$_1$-C$_6$alkyl, —S—C$_1$-C$_6$alkyl or —CF$_3$;

substituted cycloalkyl substituents of R$_{11}$' and R$_{12}$' are substituted by one or more substituents selected from a C$_1$-C$_{10}$ alkene; C$_1$-C$_6$alkyl; halogen; OH; —O—C$_1$-C$_6$alkyl; —S—C$_1$-C$_6$alkyl or —CF$_3$;

substituted phenyl or aryl of R$_{11}$' and R$_{12}$' are substituted by one or more substituents selected from halogen; hydroxy; C$_1$-C$_4$ alkyl; C$_1$-C$_4$ alkoxy; nitro; —CN; —O—C(O)—C$_1$-C$_4$alkyl and —C(O)—O—C$_1$-C$_4$-aryl; and wherein het is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S, which heterocyclic ring or fused ring system is unsubstituted or substituted on a carbon or nitrogen atom; and (b) an immune cell, wherein the compound of Formula II is capable of enhancing an immune activity of the immune cell activity.

3. The immune enhancing complex of claim 1, wherein the compound of Formula I is N-[1-cyclohexyl-2-oxo-2-(6-phenethyl-octahydro-pyrrolo[2,3-c]pyridin-1-yl)-ethyl]-2-methylamino-propionamide.

4. A pharmaceutical composition comprising:
(a) a compound of Formula I:

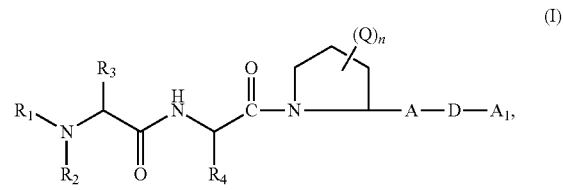

or pharmaceutically acceptable salts, enantiomers, stereoisomers, rotamers, tautomers, diastereomers, or racemates thereof;

wherein

R$_1$ is H, C$_1$-C$_4$ alkyl, C$_2$-C$_4$ alkenyl, C$_2$-C$_4$ alkynyl or C$_3$-C$_{10}$ cycloalkyl, wherein R$_1$ may be unsubstituted or substituted;

R$_2$ is H, C$_1$-C$_4$ alkyl, C$_2$-C$_4$ alkenyl, C$_2$-C$_4$ alkynyl, C$_3$-C$_{10}$ cycloalkyl, wherein R$_2$ may be unsubstituted or substituted;

R$_3$ is H, CF$_3$, C$_2$F$_5$, C$_1$-C$_4$ alkyl, C$_2$-C$_4$ alkenyl, C$_2$-C$_4$ alkynyl, CH$_2$—Z, or R$_2$ and R$_3$, taken together with the nitrogen atom to which they are attached, form a heterocyclic ring, wherein the alkyl, alkenyl, alkynyl groups or het ring may be unsubstituted or substituted;

Z is H, OH, F, Cl, CH$_3$, CH$_2$C$_1$, CH$_2$F or CH$_2$OH;

R$_4$ is C$_{1-10}$ alkyl, C$_{1-10}$ alkenyl, C$_{1-10}$ alkynyl, C$_3$-C$_{10}$ cycloalkyl, wherein the C$_{1-10}$ alkyl, or cycloalkyl groups are unsubstituted or substituted;

A is het, which may be substituted or unsubstituted;

D is C$_1$-C$_7$ alkylene or C$_2$-C$_9$ alkenylene, C(O), O, NR$_7$, S(O)$_r$, C(O)—C$_1$-C$_{10}$ alkyl, O—C$_1$-C$_{10}$ alkyl, S(O)$_r$—C$_1$-C$_{10}$ alkyl, C(O)C$_0$-C$_{10}$ arylalkyl, OC$_0$-C$_{10}$ arylalkyl, or S(O)$_r$C$_0$-C$_{10}$ arylalkyl, wherein alkyl and aryl groups may be unsubstituted or substituted;

r is 0, 1 or 2;

A$_1$ is a substituted or unsubstituted aryl or unsubstituted or substituted het, wherein substituents on aryl and het are halo, alkyl, lower alkoxy, NR$_5$R$_6$, CN, NO$_2$ or SR$_5$;

each Q is independently H, C$_1$-C$_{10}$ alkyl, C$_1$-C$_{10}$ alkoxy, aryl C$_1$-C$_{10}$ alkoxy, OH, O—C$_1$-C$_{10}$ alkyl, (CH$_2$)$_{0-6}$—C$_3$-C$_7$ cycloalkyl, aryl, aryl C$_1$-C$_{10}$ alkyl, O—(CH$_2$)$_{0-6}$ aryl, (CH$_2$)$_{0-6}$ het, het, O—(CH$_2$)$_{0-6}$ het, C(O)R$_{11}$, —C(O)N(R$_{11}$)(R$_{12}$), N(R$_{11}$)(R$_{12}$), SR$_{11}$, S(O)R$_{11}$, S(O)$_2$ R$_{11}$, S(O)$_2$—N(R$_{11}$)(R$_{12}$), or NR$_{11}$—S(O)$_2$—(R$_{12}$), wherein alkyl, cycloalkyl and aryl are unsubstituted or substituted;

n is 0, 1, 2 or 3, 4, 5, 6 or 7;

$R_{11}$ and $R_{12}$ are independently H, $C_1$-$C_{10}$ alkyl, $(CH_2)_{0-6}$—$C_3$-$C_7$ cycloalkyl, $(CH_2)_{0-6}$—$(CH)_{0-1}$ $(aryl)_{1-2}$, C(O)—$C_1$-$C_{10}$ alkyl, —C(O)—$(CH_2)_{1-6}$—$C_3$-$C_7$ cycloalkyl, —C(O)—O—$(CH_2)_{0-6}$-aryl, —C(O)—$(CH_2)_{0-6}$—O-fluorenyl, C(O)—NH—$(CH_2)_{0-6}$-aryl, C(O)—$(CH_2)_{0-6}$-aryl, C(O)—$(CH_2)_{1-6}$-het, —C(S)—$C_1$-$C_{10}$alkyl, —C(S)—$(CH_2)_{1-6}$—$C_3$-$C_7$ cycloalkyl, —C(S)—O—$(CH_2)_{0-6}$-aryl, —C(S)—$(CH_2)_{0-6}$—O-fluorenyl, C(S)—NH—$(CH_2)_{0-6}$-aryl, —C(S)—$(CH_2)_{0-6}$-aryl or C(S)—$(CH_2)_{1-6}$-het, C(O)$R_{15}$, C(O)$NR_{15}R_{16}$, C(O)OR$_{15}$, S(O)$_m R_{15}$, S(O)$_m NR_{15}R_{16}$, m=1 or 2, C(S)$R_{15}$, C(S)$NR_{15}R_{16}$, C(S)OR$_{15}$, wherein alkyl, cycloalkyl and aryl are unsubstituted or substituted; or $R_{11}$ and $R_{12}$ are a substituent that facilitates transport of the molecule across a cell membrane, or $R_{11}$ and $R_{12}$ together with the nitrogen atom form het, wherein the alkyl substituents of $R_{11}$ and $R_{12}$ may be unsubstituted or substituted by one or more substituents selected from $C_1$-$C_{10}$ alkyl, halogen, OH, O—$C_1$-$C_6$ alkyl, —S—$C_1$-$C_6$ alkyl, $CF_3$ or $NR_{15}R_{16}$;

substituted cycloalkyl substituents of $R_{11}$ and $R_{12}$ are substituted by one or more substituents selected from a $C_2$-$C_{10}$ alkene; $C_1$-$C_6$ alkyl; halogen; OH; O—$C_1$-$C_6$ alkyl; S—$C_1$-$C_6$ alkyl, $CF_3$; or $NR_{15}R_{16}$ and substituted het or substituted aryl of $R_{11}$ and $R_{12}$ are substituted by one or more substituents selected from halogen, hydroxy, $C_1$-$C_4$ alkyl, $C_1$-$C_4$ alkoxy, nitro, CNO—C(O)—$C_1$-$C_4$alkyl and C(O)—O—$C_1$-$C_4$-alkyl;

$R_5$, $R_6$ and $R_7$ are independently hydrogen, lower alkyl, aryl, aryl lower alkyl, cycloalkyl, or cycloalkyl lower alkyl, C(O)$R_{15}$, S(O)$R_{15}$, C(O)OR$_{15}$, C(O)NR$_{15}R_{16}$; and the substituents on $R_1$, $R_2$, $R_3$, $R_4$, Q, and A and Ai groups are independently halo, hydroxy, lower alkyl, lower alkenyl, lower alkynyl, lower alkanoyl, lower alkoxy, aryl, aryl lower alkyl, amino, amino lower alkyl, diloweralkylamino, lower alkanoyl, amino lower alkoxy, nitro, cyano, cyano lower alkyl, carboxy, lower carbalkoxy, lower alkanoyl, aryloyl, lower arylalkanoyl, carbamoyl, N-mono- or N,N-dilower alkyl carbamoyl, lower alkyl carbamic acid ester, amidino, guanidine, ureido, mercapto, sulfo, lower alkylthio, sulfoamino, sulfonamide, benzosulfonamide, sulfonate, sulfanyl lower alkyl, aryl sulfonamide, halogen substituted aryl sulfonate, lower alkylsulfinyl, arylsulfinyl; aryl-lower alkylsulfinyl, lower alkylarylsulfinyl, lower alkylsulfonyl, arylsulfonyl, aryl-lower alkylsulfonyl, lower aryl alkyl lower alkylarylsulfonyl, halogen-lower alkylmercapto, halogen-lower alkylsulfonyl, phosphono (—P(═O)(OH)$_2$), hydroxy-lower alkoxy phosphoryl or di-lower alkoxyphosphoryl, (R$_9$)NC(O)—NR$_{10}R_{13}$, lower alkyl carbamic acid ester or carbamates or —NR$_8 R_{14}$, wherein $R_8$ and $R_{14}$ can be the same or different and are independently H or lower alkyl, or $R_8$ and $R_{14}$, together with the N atom, form a 3- to 8-membered heterocyclic ring containing nitrogen heteroring atoms and may optionally contain one or two additional heteroring atoms selected from nitrogen, oxygen and sulfur, wherein the heterocyclic ring may be unsubstituted or substituted with lower alkyl, halo, lower alkenyl, lower alkynyl, hydroxy, lower alkoxy, nitro, amino, lower alkyl, amino, diloweralkyl amino, cyano, carboxy, lower carbalkoxy, formyl, lower alkanoyl, oxo, carbarmoyl, N-lower or N,N-dilower alkyl carbamoyl, mercapto, or lower alkylthio;

$R_9$, $R_{10}$ and $R_{13}$ are independently hydrogen, lower alkyl, halogen substituted lower alkyl, aryl, aryl lower alkyl, halogen substituted aryl, halogen substituted aryl lower alkyl;

wherein $R_{15}$ and $R_{16}$ are independently hydrogen, lower alkyl, aryl, aryl lower alkyl, cycloalkyl, or cycloalkyl lower alkyl; and het is a 5- to 7-membered monocyclic heterocyclic ring containing 1-4 heteroring atoms selected from N, O and S or an 8- to 12-membered fused ring system that includes one 5- to 7-membered monocyclic heterocyclic ring containing 1, 2 or 3 heteroring atoms selected from N, O and S, wherein het is unsubstituted or substituted; and (b) an antigen, wherein the antigen comprises an antigen present in a cancer cell, a cancer cell, a cancer cell fragment, a tumor antigen, α-galcer, anti-CD3, anti-CD28, anti-IgM, anti-CD40, a pathogen, an attenuated pathogen, or a portion thereof, wherein the compound of Formula I is capable of enhancing an immune response of a subject to the antigen activity of the composition is synergistically enhanced compared to activity of (b), alone.

5. A pharmaceutical composition comprising:
(a) a compound of Formula II:

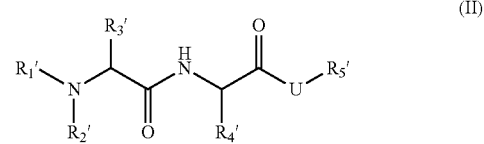

and pharmaceutically acceptable salts, enantiomers, stereoisomers, rotamers, tautomers, diastereomers, or racemates thereof;
wherein
$R_1'$ is H;
$R_2'$ is $C_1$-$C_4$ alkyl; which may be unsubstituted or substituted;
$R_3'$ is $C_1$-$C_4$ alkyl;
$R_4'$ is —$C_3$-$C_{10}$cycloalkyl; which may be unsubstituted or substituted;
$R_5'$ is H; $C_1$-$C_{10}$-alkyl; aryl; phenyl; $C_3$-$C_7$cycloalkyl; —$(CH_2)_{1-6}$—$C_3$-$C_7$cycloalkyl; —$C_1$-$C_{10}$alkyl-aryl; —$(CH_2)_{0-6}$—$C_3$-$C_7$cycloalkyl-$(CH_2)_{0-6}$-phenyl; —$(CH_2)_{0-4}$CH—$((CH_2)_{1-4}$-phenyl)$_2$; —$(CH_2)_{0-6}$—CH(phenyl)$_2$, -indanyl; —C(O)—$C_1$-$C_{10}$alkyl; —C(O)—$(CH_2)_{1-6}$—$C_3$-$C_7$-cycloalkyl; —C(O)—$(CH_2)_{0-6}$-phenyl; —$(CH_2)_{0-6}$—C(O)-phenyl; —$(CH_2)_{0-6}$-het; —C(O)—$(CH_2)_{1-6}$-het; or $R_5'$ is a residue of an amino acid, wherein the alkyl, cycloalkyl, phenyl and aryl substituents are unsubstituted or substituted;
U is as shown in structure III:

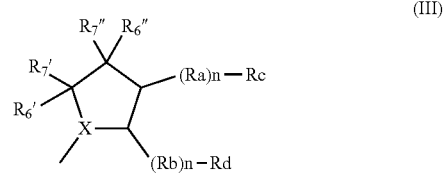

wherein $R_5'$ is attached to Rc or Rd;
each n is, independently, 0-5;
X is C or N;
Ra and Rb are independently an O, S, or N atom or $C_{0-8}$ alkyl wherein one or more of the carbon atoms in the alkyl chain may be replaced by a heteroatom selected from O, S or N, and where the alkyl may be unsubstituted or substituted;

Rd is selected from:
(a) -Re-Q-(Rf)$_p$(Rg)$_q$; or
(b) $Ar_1$-D-$Ar_2$;
Rc is H or Rc and Rd may together form a cycloalkyl or het; where if Rd and Rc form a cycloalkyl or het, $R_5'$ is attached to the formed ring at a C or N atom;
p and q are independently 0 or 1;
Re is $C_{1-8}$ alkyl or alkylidene, and Re which may be unsubstituted or substituted;
Q is N, O, S, S(O), or S(O)$_2$;
$Ar_1$ and $Ar_2$ are substituted or unsubstituted aryl or het;
Rf and Rg are each independently H; —$C_1$-$C_{10}$alkyl; $C_1$-$C_{10}$alkylaryl; —OH; —O—$C_1$-$C_{10}$alkyl; —(CH$_2$)$_{0-6}$—$C_3$-$C_7$cycloalkyl; —O—(CH$_2$)$_{0-6}$-aryl; phenyl; aryl; phenyl-phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S(O)—R$_{11}$; —S(O)$_2$—R$_{11}$; —S(O)$_2$—NR$_{11}$R$_{12}$; —NR$_{11}$—S(O)$_2$—R$_{12}$; S—$C_1$-$C_{10}$alkyl; aryl-$C_1$-$C_4$alkyl; het-$C_1$-$C_4$alkyl wherein alkyl, cycloalkyl, het and aryl are unsubstituted or substituted; —SO$_2$—$C_1$-$C_2$alkyl; —SO$_2$—$C_1$-$C_2$alkylphenyl; —O—$C_1$-$C_4$alkyl; or R$_g$ and R$_f$ form a ring selected from het or aryl;
D is —CO—; —C(O)—$C_{1-7}$ alkylene or arylene; —CF$_2$—; —O—; —S(O)$_r$ where r is 0-2; 1,3-dioxolane; or $C_{1-7}$ alkyl-OH; where alkyl, alkylene or arylene may be unsubstituted or substituted with one or more halogens, OH, —O—$C_1$-$C_6$alkyl, —S—$C_1$-$C_6$alkyl or —CF$_3$; or D is —N(Rx)- wherein Rx is H; $C_{1-7}$ alkyl (unsubstituted or substituted); aryl; —O($C_{1-7}$cycloalkyl) (unsubstituted or substituted); C(O)—$C_1$-$C_{10}$alkyl; C(O)—$C_0$-$C_{10}$alkyl-aryl; C—O—$C_1$-$C_{10}$alkyl; C—O—$C_0$-$C_{10}$alkyl-aryl or SO$_2$—$C_1$-$C_{10}$alkyl; SO$_2$—($C_0$-$C_{10}$-alkylaryl);
$R_6''$, $R_7''$, $R_6'$ and $R_7'$ are each independently H; —$C_1$-$C_{10}$ alkyl; —$C_1$-$C_{10}$ alkoxy; aryl-$C_1$-$C_{10}$ alkoxy; —OH; —O—$C_1$-$C_{10}$alkyl; —(CH$_2$)$_{0-6}$—$C_3$-$C_7$cycloalkyl; —O—(CH$_2$)$_{0-6}$-aryl; phenyl; —(CH$_2$)$_{1-6}$-het; —O—(CH$_2$)$_{1-6}$-het; —OR$_{11}$'; —C(O)—N(R$_{11}$')(R$_{12}$'); —N(R$_{11}$')(R$_{12}$'); —S—R$_{11}$'; —S(O)$_2$—R$_{11}$'; —NR$_{11}$'—S(O)$_2$—R$_{12}$; wherein alkyl, cycloalkyl and aryl are unsubstituted or substituted; and $R_6''$, $R_7''$, $R_6'$ and $R_7'$ can be united to form a ring system;
$R_{11}'$ and $R_{12}'$ are independently H; $C_1$-$C_{10}$ alkyl; —(CH$_2$)$_{0-6}$—$C_3$-$C_7$cycloalkyl; —(CH$_2$)$_{0-6}$—(CH)$_{0-1}$(aryl)$_{1-2}$; —C(O)—$C_1$-$C_{10}$alkyl; —C(O)—(CH$_2$)$_{1-6}$—$C_3$-$C_7$cycloalkyl; —C(O)—O—(CH$_2$)$_{0-6}$-aryl; —C(O)—(CH$_2$)$_{0-6}$—O-fluorenyl; —C(O)—NH—(CH$_2$)$_{0-6}$-aryl; —C(O)—(CH$_2$)$_{0-6}$-aryl; —C(O)—(CH$_2$)$_{1-6}$-het; —C(S)—$C_1$-$C_{10}$alkyl; —C(S)—(CH$_2$)$_{1-6}$—$C_3$-$C_7$cycloalkyl; —C(S)—O—(CH$_2$)$_{0-6}$-aryl; —C(S)—(CH$_2$)$_{0-6}$—O-fluorenyl; —C(S)—NH—(CH$_2$)$_{0-6}$-aryl; —C(S)—(CH$_2$)$_{0-6}$-aryl; —C(S)—(CH$_2$)$_{1-6}$-het; wherein alkyl, cycloalkyl and aryl are unsubstituted or substituted; or $R_{11}'$ and $R_{12}'$ are a substituent that facilitates transport of the molecule across a cell membrane; or $R_{11}'$ and $R_{12}'$ together with the nitrogen atom form het;

wherein the alkyl substituents of $R_{11}'$ and $R_{12}'$ may be unsubstituted or substituted by one or more substituents selected from $C_1$-$C_{10}$alkyl, halogen, OH, —O—$C_1$-$C_6$alkyl, —S—$C_1$-$C_6$alkyl or —CF$_3$;
substituted cycloalkyl substituents of $R_{11}'$ and $R_{12}'$ are substituted by one or more substituents selected from a $C_1$-$C_{10}$ alkene; $C_1$-$C_6$alkyl; halogen; OH; —O—$C_1$-$C_6$alkyl; —S—$C_1$-$C_6$alkyl or —CF$_3$;
substituted phenyl or aryl of $R_{11}'$ and $R_{12}'$ are substituted by one or more substituents selected from halogen; hydroxy; $C_1$-$C_4$ alkyl; $C_1$-$C_4$ alkoxy; nitro; —CN; —O—C(O)—$C_1$-$C_4$alkyl and —C(O)—O—$C_1$-$C_4$-aryl; and wherein het is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S, which heterocyclic ring or fused ring system is unsubstituted or substituted on a carbon or nitrogen atom; and (b) an antigen, wherein the antigen comprises an antigen present in a cancer cell, a cancer cell, a cancer cell fragment, a tumor antigen, α-galcer, anti-CD3, anti-CD28, anti-IgM, anti-CD40, a pathogen, an attenuated pathogen, or a portion thereof, wherein the compound of Formula II is capable of enhancing an immune response of a subject to the antigen.

6. The pharmaceutical composition of claim 4, wherein the compound of Formula I is N-[1-cyclohexyl-2-oxo-2-(6-phenethyl-octahydro-pyrrolo[2,3-c]pyridin-1-yl)-ethyl]-2-methylamino-propionamide.

\* \* \* \* \*